US009289252B2

(12) United States Patent
Dacosta et al.

(10) Patent No.: US 9,289,252 B2
(45) Date of Patent: Mar. 22, 2016

(54) ORTHOPAEDIC PLATE AND SPREADER APPARATUSES AND METHODS

(75) Inventors: Albert Dacosta, Fort Collins, CO (US); Matthew S. Solar, Indiatlantic, FL (US); Thomas Sangiovanni, Miami, FL (US); William Krauss, Birmingham, AL (US)

(73) Assignee: PARAGON 28, INC., Englewood, CO (US)

( * ) Notice: Subject to any disclaimer, the term of this patent is extended or adjusted under 35 U.S.C. 154(b) by 179 days.

(21) Appl. No.: 14/110,571

(22) PCT Filed: Apr. 9, 2012

(86) PCT No.: PCT/US2012/032776
§ 371 (c)(1),
(2), (4) Date: Dec. 20, 2013

(87) PCT Pub. No.: WO2013/062621
PCT Pub. Date: May 2, 2013

(65) Prior Publication Data
US 2014/0107650 A1    Apr. 17, 2014

Related U.S. Application Data

(60) Provisional application No. 61/473,195, filed on Apr. 8, 2011, provisional application No. 61/473,200, filed on Apr. 8, 2011.

(51) Int. Cl.
*A61B 17/66*    (2006.01)
*A61B 17/80*    (2006.01)

(52) U.S. Cl.
CPC ........... *A61B 17/8009* (2013.01); *A61B 17/808* (2013.01)

(58) Field of Classification Search
CPC combination set(s) only.
See application file for complete search history.

(56) References Cited

U.S. PATENT DOCUMENTS

| 5,827,286 A | 10/1998 | Incavo et al. |
| 5,902,304 A | 5/1999 | Walker et al. |
| 7,641,675 B2 * | 1/2010 | Lindemann ........ A61B 17/7059 606/280 |
| 2007/0213729 A1 | 9/2007 | Lindemann et al. |
| 2008/0147125 A1 | 6/2008 | Colleran et al. |

(Continued)

FOREIGN PATENT DOCUMENTS

FR    2720623 A1    12/1995

OTHER PUBLICATIONS

International Search Report for PCT/US2012/032776 dated May 15, 2013.
Ribeiro, et al; "A new fixation material for open-wedge tibial osteotomy for genu varum," The Knee, 2009, vol. 16, Issue 5, pp. 366-370.

(Continued)

*Primary Examiner* — Sameh Boles
(74) *Attorney, Agent, or Firm* — Heslin Rothenberg Farley & Mesiti P.C.

(57) ABSTRACT

Orthopaedic plate and spreader apparatuses and methods for distracting and compressing bones and fractured bones in a patient. A first orthopaedic plate and tab assembly has ratcheting teeth on the plate and tab for distracting two bone surfaces to a desire wedge shape. The plate may have longitudinal and diametral curvatures. A second orthopaedic plate and tab assembly has a female plate with ratcheting teeth configured to mate with a male plate with ratcheting teeth for compression and distraction of two bone surfaces. The ratcheting teeth of the first and second orthopaedic plate and tab assemblies may be one way ratcheting teeth or two way ratcheting teeth. Surgical methods for inserting the implants within the patient.

21 Claims, 35 Drawing Sheets

(56) References Cited

U.S. PATENT DOCUMENTS

| | | |
|---|---|---|
| 2009/0012529 A1 | 1/2009 | Blain et al. |
| 2010/0121329 A1 | 5/2010 | Ryan et al. |
| 2010/0145386 A1 | 6/2010 | Greenhalgh et al. |
| 2010/0198221 A1 | 8/2010 | Hearn |
| 2010/0249934 A1 | 9/2010 | Melkent |

OTHER PUBLICATIONS

International Preliminary Report on Patentability for corresponding PCT application No. PCT/US2012/032776, mailed on Oct. 17, 2013.
Sep. 1, 2015: Supplementary European Search Report for European Application No. 12842779.6.

* cited by examiner

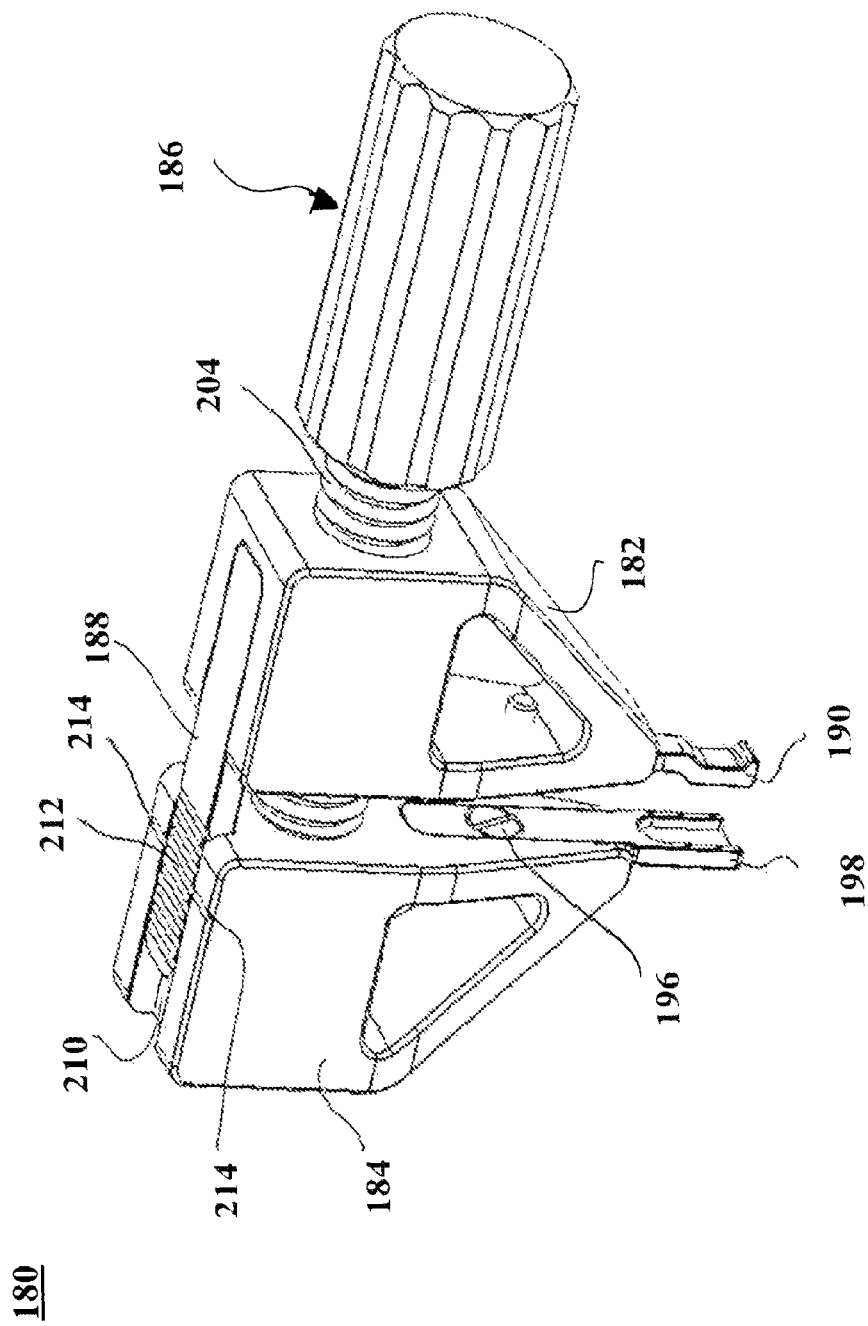

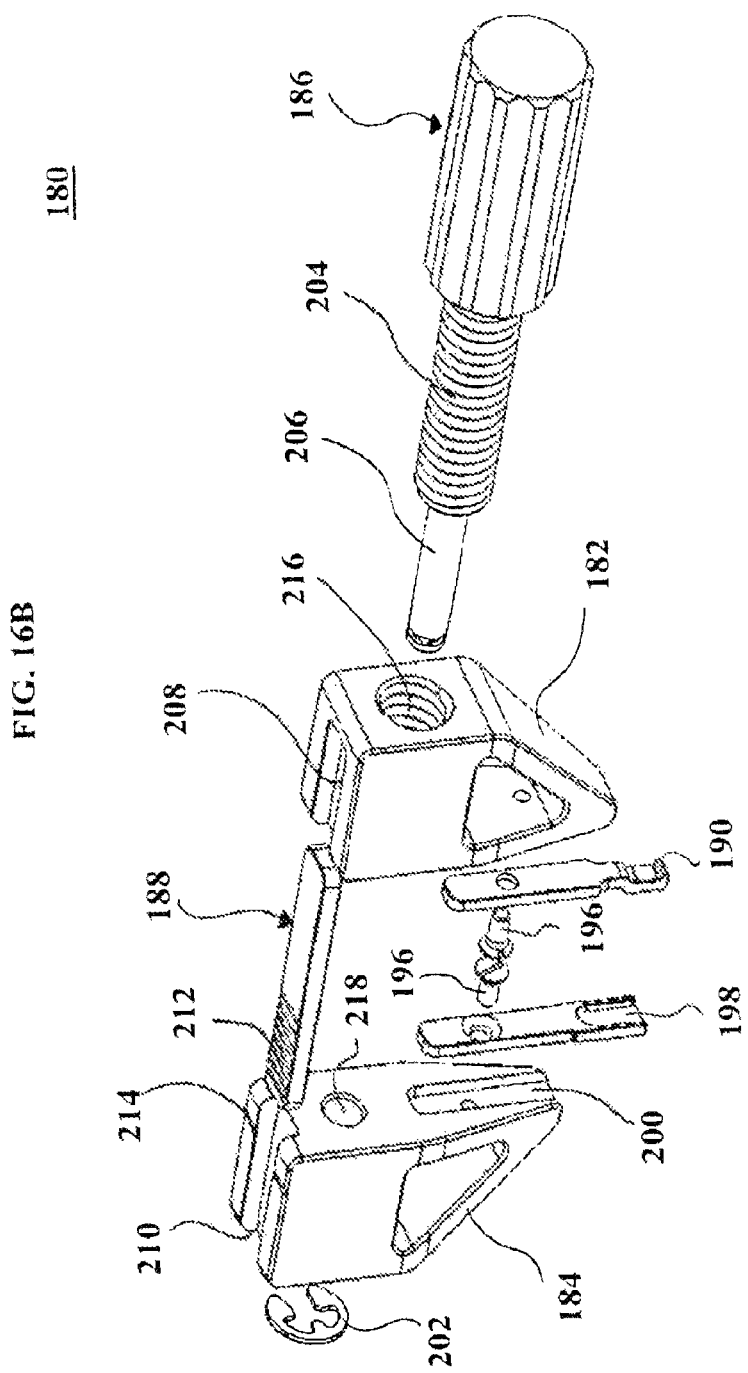

ORTHOPAEDIC PLATE AND SPREADER APPARATUSES AND METHODS

CROSS REFERENCE TO RELATED APPLICATIONS

This application is a national stage filing under section 371 of International Application No. PCT/US2012/032776 filed on Apr. 9, 2012, and published in English on May 2, 2013 as WO 2013/062621 A2 and claims priority benefit under 35 U.S.C. §119(e) to U.S. provisional patent application No. 61/473,195 filed Apr. 8, 2011 and U.S. provisional patent application No. 61/473,200 filed Apr. 8, 2011, the entire disclosure of these applications being hereby incorporated herein by reference.

TECHNICAL FIELD

This present disclosure relates generally to the field of orthopaedics related to ratcheting plates and spreaders.

BACKGROUND

Currently surgeons perform an opening wedge procedure to correct an angular deformity of a bone by making a partial cut in a first bone, for example a metatarsal, and preserving the lateral cortex of the bone. Once the surgeon creates the opening wedge, the size of the block to be inserted is determined. In order to determine the appropriate sized block, the surgeon will generally use a measuring device. The surgeon will initially select a first size block, insert the first size block into the opening, and measure the length. The surgeon may then try other sizes of blocks in the opening which result in the bone cut being repeatedly opened and then closed. With the repeated opening and closing of the bones the lateral cortex of the bone is likely to crack and compromise the hinge that the surgeon created between the two bone surfaces. This loss of the hinge between the cut bones will result in the loss of all stability between the two bones leading to distraction of the toe and malalignment.

SUMMARY

The present invention is directed toward devices, instruments, and methods for expanding and compressing the space between bones.

In one aspect of the present invention provided herein, the ratcheting plate and spreader devices, instruments, and methods are used for correction of the hallux valgus deformity at the base of the first metatarsal using an opening wedge procedure. The device and instrumentation enable precise and gradual correction of the deformity while minimizing the risk associated with fracture of the lateral cortex and subsequent destabilization.

In another aspect of the present invention provided herein, the ratcheting plate and spreader devices, instruments, and methods are used for compression of an osteotomy or fracture to create an appropriate environment for healing to occur. The device will prevent release of compression via ratcheting teeth of the female plate engaging with the ratcheting teeth of the male plate. The device and instrumentation enable precise compression, appropriate for the differing degrees of bone quality encountered during surgery. The ratcheting teeth may allow for small increments of compression, such as 0.5 mm. The teeth may be shaped and designed to allow movement in only one direction or in both directions.

In one aspect of the present invention provided herein, is an orthopaedic plate system for insertion into a patient's joint. The plate system has a plate and a tab. The plate has a proximal end and a distal end with a central portion extending between the proximal end and the distal end wherein the plate has a first opening in the central portion, a first pair of arms at a proximal end, and a second pair of arms at a distal end. The tab has a body with a first arm and a second arm. The tab is configured to mate with the first opening of the plate. The first opening of the plate may have a generally rectangular shape and a row of teeth on each longitudinal edge. The tab may have a row of teeth on the first and second arms which engage the teeth on the longitudinal edges of the first opening of the plate. The plate may have a longitudinal curvature along a longitudinal axis and/or a diametral curvature along a lateral axis.

In another embodiment of the present invention provided herein, is a surgical method for implanting the orthopaedic plate system in a patient. The method includes exposing a first bone surface and a second bone surface of the patient. The plate system is then inserted into the patient with the tab being inserted between the first and second bone surfaces. The first end of the plate system may then be attached in a first position to the first bone surface. The plurality of teeth of the first and second arms of the tab may then be ratcheted over the two rows of teeth of the plate to apply a force on the second bone surface. The force on the second bone surface may distract the second bone surface away from the first bone surface and to a final position. After the final position is achieved the second end of the plate system may be attached to the second bone surface. Finally, the tab may optionally be removed from the plate.

In a further aspect of the present invention provided herein, is an orthopaedic plate system which has a curved plate with a proximal end and a distal end. The curved plate has a central portion extending between the proximal end and the distal end with a first opening in the central portion, a first pair of arms at a proximal end, and a second pair of arms at a distal end. The plate system may also have a notch in the first opening that is configured to mate with a tool. The tool may have a first and second tip use with the plate to distract a first bone surface from a second bone surface.

In yet another aspect of the present invention provided herein, is an orthopaedic plate system which has a curved plate, an insert plate, and a tab. The curved plate has a proximal end and a distal end. The curved plate also has a central portion extending between the proximal end and distal end with a first opening, a first pair of arms at a proximal end, and a second pair of arms at a distal end. The insert plate may have teeth which engage with teeth in the first opening of the curved plate. The tab may be coupled to the plate with a fastener and is inserted between a first bone and a second bone.

In another aspect of the present invention provided herein, is a surgical method for implanting a plate system, which has a plate with a first opening and a notch and a tool with a first tip and a second tip, into a patient. The method including exposing a first bone surface and a second bone surface of the patient. The plate system is then inserted into the patient and a first end of the plate system is attached to the first bone surface. The tool may then be inserted between the first and second bone surfaces and the first tip may mate with the notch of the plate and the second tip may mate with the second bone surface. Then a force may be applied to the tool to separate the first tip and second tip thereby applying a force on the second bone surface to distract the second bone surface from the first bone surface to a final position. When a final position is achieved a second end of the plate system may be attached to the second bone surface.

In a further aspect of the present invention provided herein, is a surgical method for implanting a plate system, which has an elongated plate with two rows of teeth on a longitudinal edge of the plate opening, an insert plate with a plurality of teeth configured to engage the teeth on the elongated plate, and a tab configured for attachment to the insert plate, into a patient. The method including exposing a first bone surface and a second bone surface of the patient. The plate system is then inserted into the patient with the tab being inserted between the first and second bone surfaces. The first end of the plate system is then attached to the first bone surface. The plurality of teeth of the insert plate may then be ratcheted over the teeth of the elongate plate to apply a force on the second bone surface with the tab to distract the second bone surface from the first bone surface to a final position. Then the second end of the plate system may be attached to the second bone surface in the final position. Optionally, the insert plate and tab may then be removed from the elongate plate.

Yet a further embodiment of the present invention provided herein, is an orthopaedic plate assembly with a male plate and a female plate. The male plate may have a base connected to a ratcheting member that has two legs separated by a slot and a plurality of teeth on the outer longitudinal edge of the two legs. The female plate may have a base with a cavity which has a plurality of teeth on at least one longitudinal edge. The teeth of the cavity may be configured to mate with the teeth of the ratcheting member. The plate assembly may be used for compression or distraction of two bone surfaces.

In still another embodiment of the present invention provided herein, is an orthopaedic plate assembly with a male plate and a female plate. The male plate may have a base with a plurality of teeth on at least one edge. The female plate may have a base, two end openings, and a center opening. The center opening has a plurality of teeth on at least one longitudinal edge configured to engage the plurality of teeth on the male plate. The plate assembly may be used for compression or distraction of two bone surfaces.

In another aspect of the present invention provided herein, is a surgical method for implanting a plate system into a patient. The plate system has a female plate with a base and an opening that has a plurality of teeth along at least one longitudinal edge and a male plate with a base that has a plurality of teeth along at least one outer edge. The teeth of the female plate being configured to engage the teeth of the male plate. The method including exposing a first bone surface and a second bone surface of the patient. The plate system is then inserted into the patient. The female plate is attached to the first bone surface and the male plate is attached to the second bone surface. A force may then be applied to the male and female plates to move the first and second bone surfaces to a final position. The force applied to the male and female plates may be done using a tool. The plate assembly may be used for compression or distraction of two bone surfaces.

These and other objects, features and advantages of this invention will become apparent from the following detailed description of the various aspects of the invention taken in conjunction with the accompanying drawings.

BRIEF DESCRIPTION OF DRAWINGS

The accompanying drawings, which are incorporated in and constitute a part of the specification, illustrate embodiments of the invention and together with the detailed description herein, serve to explain the principles of the invention. It is emphasized that, in accordance with the standard practice in the industry, various features are not drawn to scale. In fact, the dimensions of the various features may be arbitrarily increased or reduced for clarity of discussion. The drawings are only for purposes of illustrating preferred embodiments and are not to be construed as limiting the invention.

FIG. 15 is an isometric view of the tool of FIGS. 13-14 in a partially extended position, in accordance with an aspect of the present invention;

FIG. 16B is an exploded left isometric view of the tool of FIGS. 13-15, in accordance with an aspect of the present invention;

DETAILED DESCRIPTION

In this application, the words proximal, distal, anterior or plantar, posterior or dorsal, medial and lateral are defined by their standard usage for indicating a particular part or portion of a bone or prosthesis coupled thereto, or directional terms of reference, according to the relative disposition of the natural bone. For example, "proximal" means the portion of a bone or prosthesis nearest the torso, while "distal" indicates the portion of the bone or prosthesis farthest from the torso. As an example of directional usage of the terms, "anterior" refers to a direction towards the front side of the body, "posterior" refers to a direction towards the back side of the body, "medial" refers to a direction towards the midline of the body and "lateral" refers to a direction towards the sides or away from the midline of the body. Further, specifically in regards to the foot, the term "dorsal" refers to the top of the foot and the term "plantar" refers the bottom of the foot.

Similarly, positions or directions may be used herein with reference to anatomical structures or surfaces. For example, as the current devices, instrumentation and methods are described herein with reference to use with the bones of the foot, the bones of the foot, ankle and lower leg may be used to describe the surfaces, positions, directions or orientations of the devices, instrumentation and methods. Further, the devices, instrumentation and methods, and the aspects, components, features and the like thereof, disclosed herein are described with respect to one side of the body for brevity purposes. However, as the human body is relatively symmetrical or mirrored about a line of symmetry (midline), it is hereby expressly contemplated that the devices, instrumentation and methods, and the aspects, components, features and the like thereof, described and/or illustrated herein may be changed, varied, modified, reconfigured or otherwise altered for use or association with another side of the body for a same or similar purpose without departing from the spirit and scope of the invention. For example, the devices, instrumentation and methods, and the aspects, components, features and the like thereof, described herein with respect to the right foot may be mirrored so that they likewise function with the left foot. Further, the devices, instrumentation and methods, and the aspects, components, features and the like thereof, disclosed herein are described with respect to the foot for brevity purposes, but it should be understood that the devices, instrumentation, and methods may be used with other bones of the body having similar structures, for example the upper extremity, and more specifically, with the bones of the wrist, hand, and arm.

Figure 1:
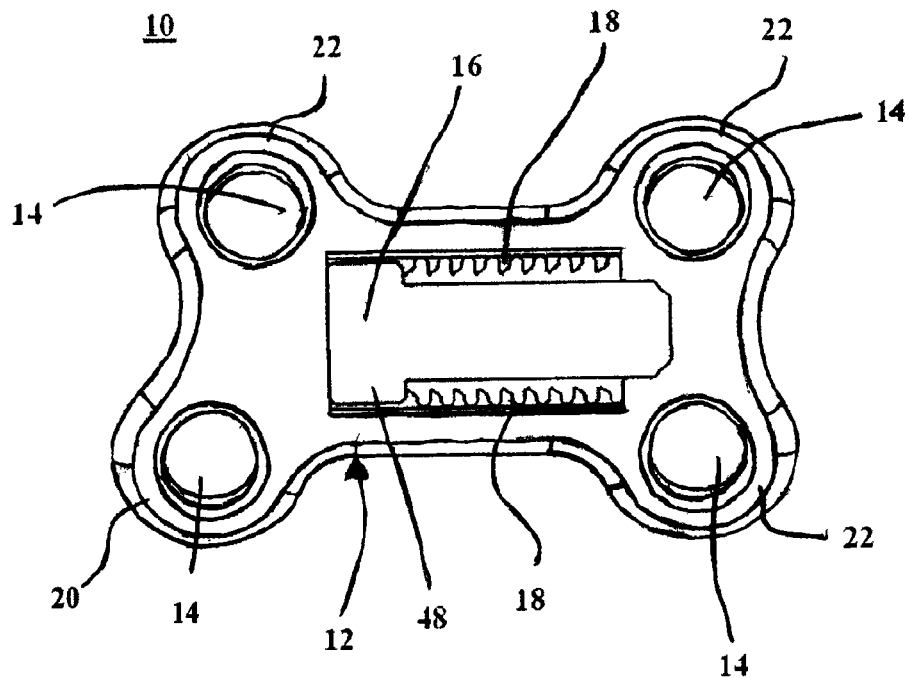
FIG. 1 is a top view of a ratcheting plate, in accordance with an aspect of the present invention.
Figure 2:
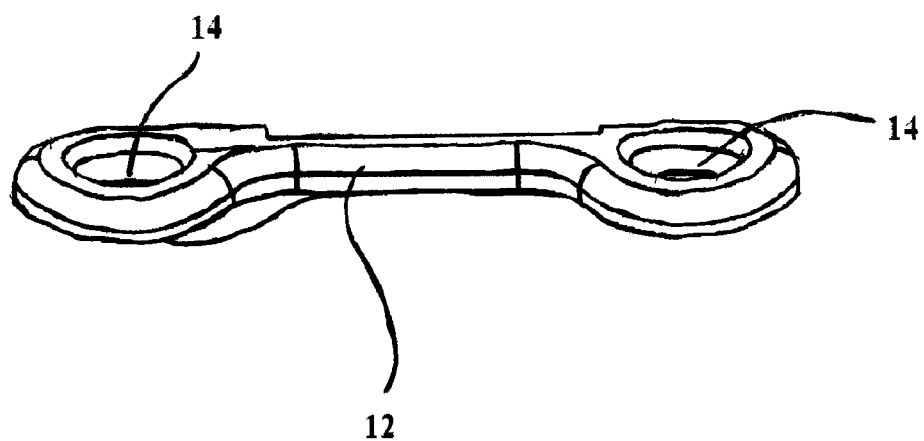
FIG. 2 is a side view of the ratcheting plate of FIG. 1, in accordance with an aspect of the present invention.
Figure 3:
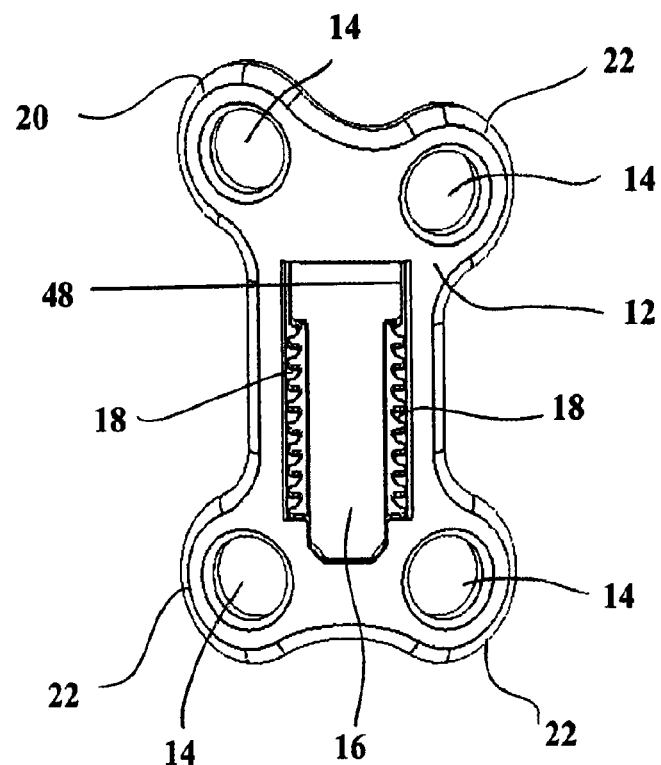
FIG. 3 is a top view of the ratcheting plate of FIGS. 1 and 2 in a vertical orientation, in accordance with an aspect of the present invention.
Figure 4:
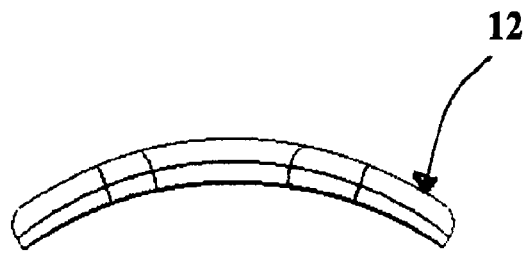
FIG. 4 is a side view of the ratcheting plate of FIGS. 1-3, in accordance with an aspect of the present invention.
Figure 5:
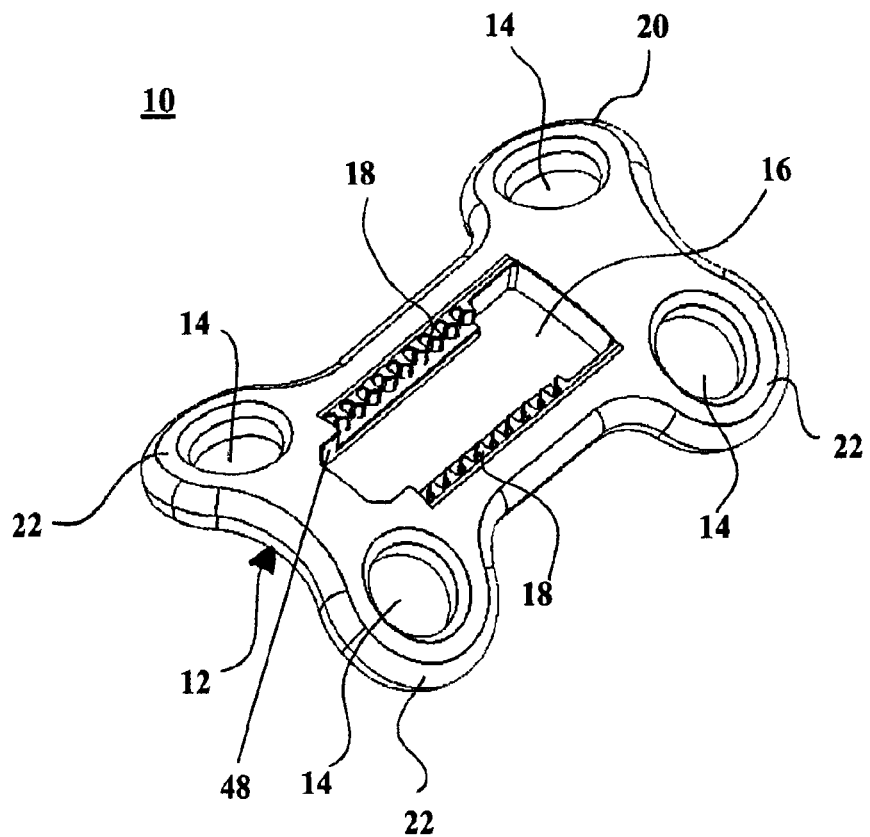
FIG. 5 is an isometric view of a ratcheting plate of FIGS. 1-4, in accordance with an aspect of the present invention.
Figure 6:
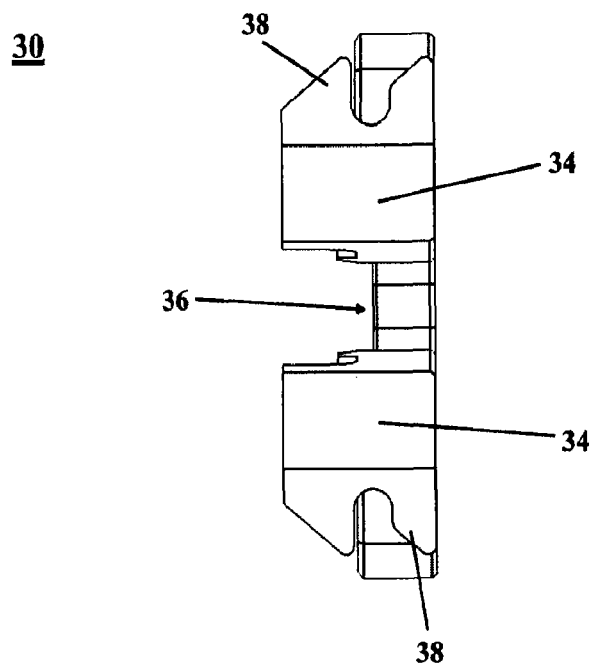
FIG. 6 is a top view of a ratcheting tab, in accordance with an aspect of the present invention.
Figure 7:
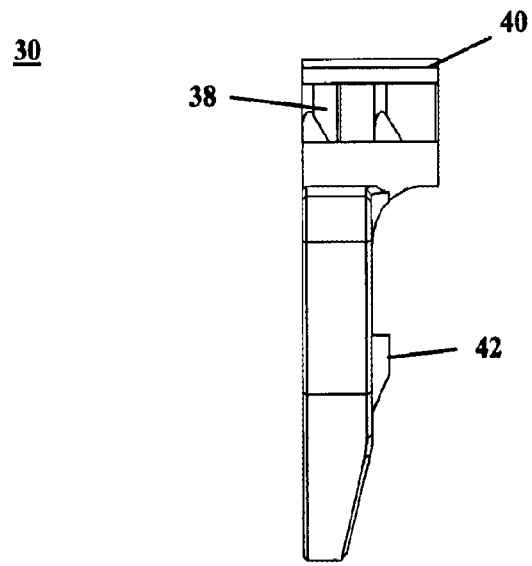
FIG. 7 is a side view of the ratcheting tab of FIG. 6, in accordance with an aspect of the present invention.

Referring to the drawings, wherein like reference numerals are used to indicate like or analogous components throughout the several views, and with particular reference to FIGS. 1-5, there is illustrated an exemplary embodiment plate 10. Referring now to FIGS. 1, 3, and 5, the plate 10 has a body 12 with one or more screw holes 14 and an opening 16. For example purposes, the plate 10 is shown as being a generally I-shaped with a generally rectangular shaped body 12 and has two pairs of rounded arms forming the top and bottom lines of the I-shape. It is also contemplated that the plate 10 may be generally H-shaped. However, other plate shapes may be used to address certain clinical situations. The first pair of rounded arms of body 12 may have a first arm 20, which is offset from a second arm 22 and the second pair of rounded arms of body 12 may have two parallel second arms 22. As depicted in FIGS. 1-5, the one or more screw holes 14 may be located in the arms 20, 22 of the body 12 wherein there are preferably four screw holes 14. The one or more screw holes 14 may be threaded or non-threaded holes. The opening 16 may be centered in the body 12 along the longitudinal axis of the plate 10. The opening 16 may also have two parallel rows of teeth 18 along the outer edges of the opening 16. As best seen in FIG. 2, the plate 10 may have a longitudinal curvature for conforming to the angle of the bone or bones it is attached to for distraction. Referring now to FIG. 4, the plate 10 may have a diametral curvature for conforming to the surface of the outer diameter of the bone or bones which the plate 10 is attached to for distraction.

Figure 8:
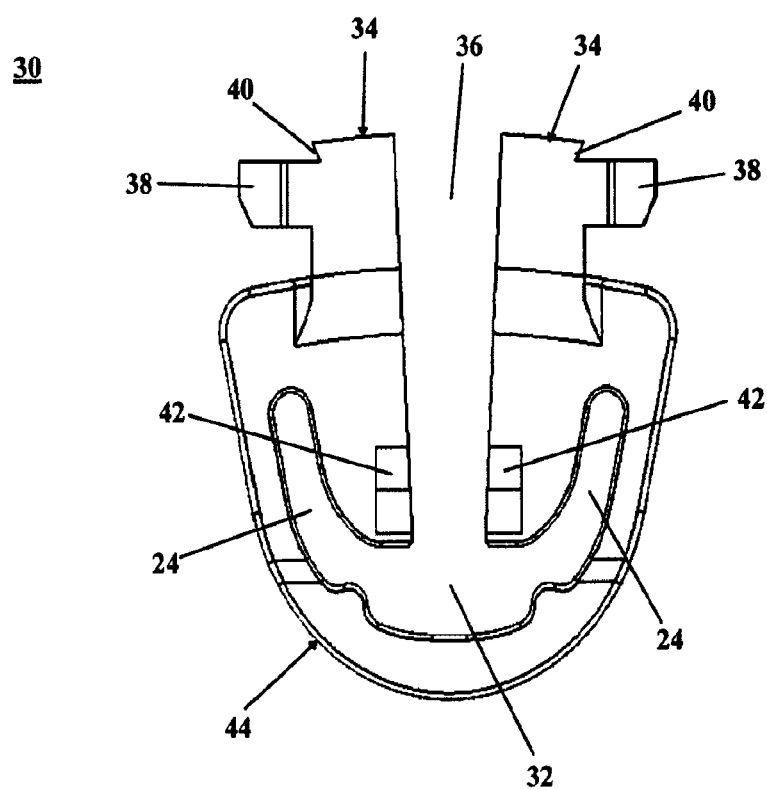
FIG. 8 is a front view of the ratcheting tab of FIGS. 6-7, in accordance with an aspect of the present invention.
Figure 9:
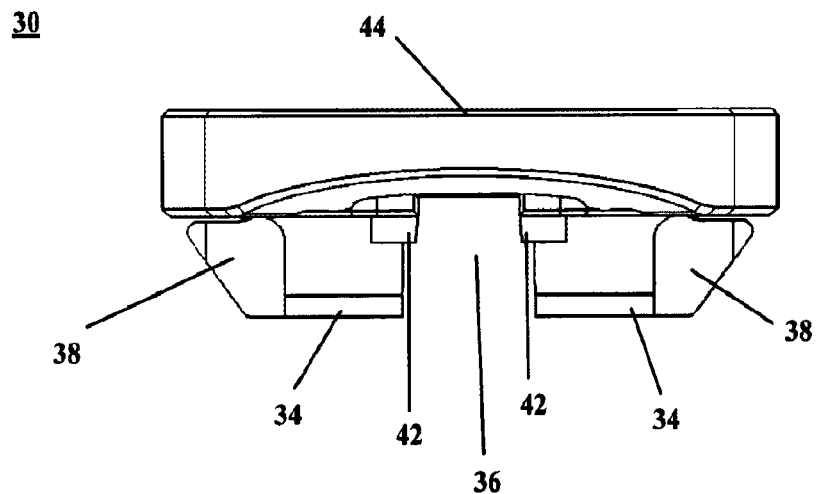
FIG. 9 is a bottom view of the ratcheting tab of FIGS. 6-8, in accordance with an aspect of the present invention.
Figure 10:
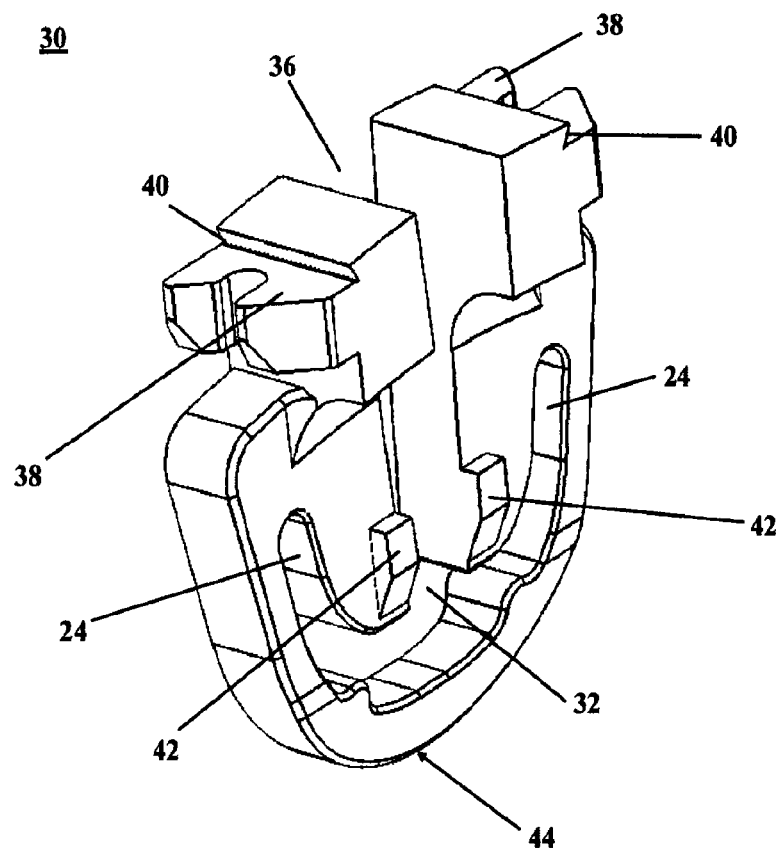
FIG. 10 is an isometric view of the ratcheting tab of FIGS. 6-9, in accordance with an aspect of the present invention.

The opening 16 of the plate 10 is configured to mate with a tab 30, illustrated in FIGS. 6-10. The tab 30 may have a central slot 32 with two arms 34 on either side of the opening 36 of the central slot 32. The arms 34 have a proximal surface for receiving a tool for actuation of the tab 30. The central slot 32 may have an opening down the center of the tab 30 and an opening along the bottom surface of the tab 30, more preferably the central slot 32 may have an opening down the center of the tab 30 and a semi-circular curve 24 along the bottom surface of the tab 30, as depicted in FIGS. 8 and 10. The ratcheting tab 30 may also have teeth 38 on the top along the outside of the two arms 34 for mating with the teeth 18 of plate 10. The two arms 34 may also have indents 40 above the teeth 38. The indents 40 may enable a tool (Not Shown), to engage the top of the tab 30 if the tab 30 is actuated too far by the surgeon and reverse the tab back towards the proximal end of the plate 10. When squeezed, the central slot 32 allows for deflection of the sides of tab 30 enabling engagement and disengagement of the teeth 38 from the teeth of the plate 10. The bottom of the teeth 38 may have a 45 degree angle to allow insertion during a compressed state. The teeth 38 may also have a first chamfered edge on the distal end of the first arm and a second chamfered edge on the proximal end of the second arm enabling the tab 30 to be inserted into plate 10 parallel to teeth 18 and then rotated 90 degrees to engage teeth 38 of the tab 30 with teeth 18 of the plate 10. The indents 40 may be used to squeeze the central slot 32 during insertion of the tab 30 from the plate 10 and when the tab 30 has been actuated to far during a procedure to reverse the tab 30 towards the initial position at the proximal end of the plate 10. Alternatively, the tab 30 may be inserted into the plate 10 at the distal end of the opening 16 where there are no teeth 18 along the longitudinal sides of the opening 16. Then the teeth 38 of the tab 30 may be aligned with the teeth 18 of the plate 10 and the tab 30 may be forced to the proximal end of the opening 16. The ratcheting tab 30 may also have protrusions 42 on either side of the central slot 32. The protrusions 42 may engage the under surface of the bone being distracted. The tab 30 may also have a tapered end 44 for facilitating the insertion of the tab 30 between two bone surfaces.

Figure 11:
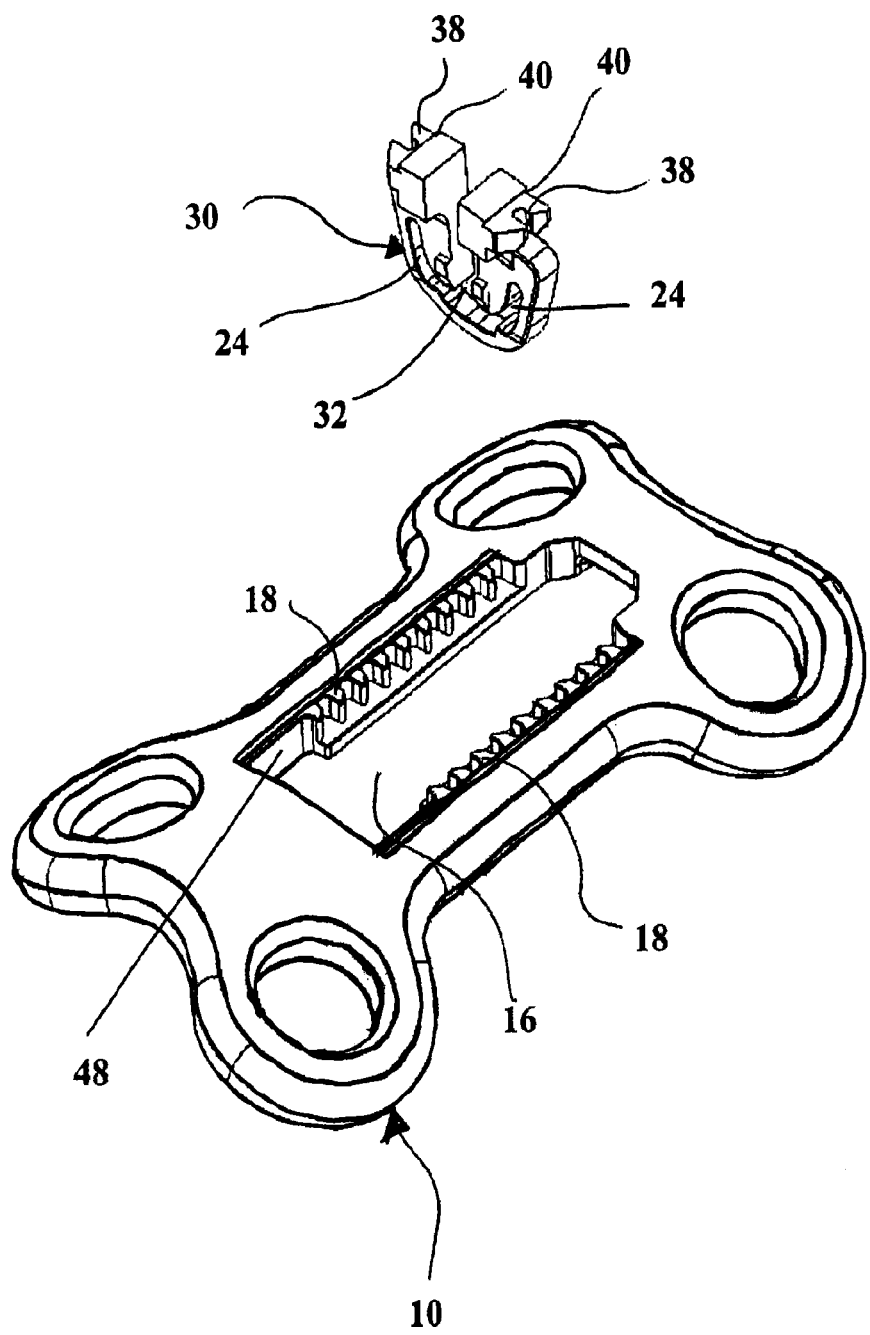
FIG. 11 is an exploded isometric view of the ratcheting plate of FIGS. 1-5 and the ratcheting tab of FIGS. 6-10, in accordance with an aspect of the present invention.
Figure 12:
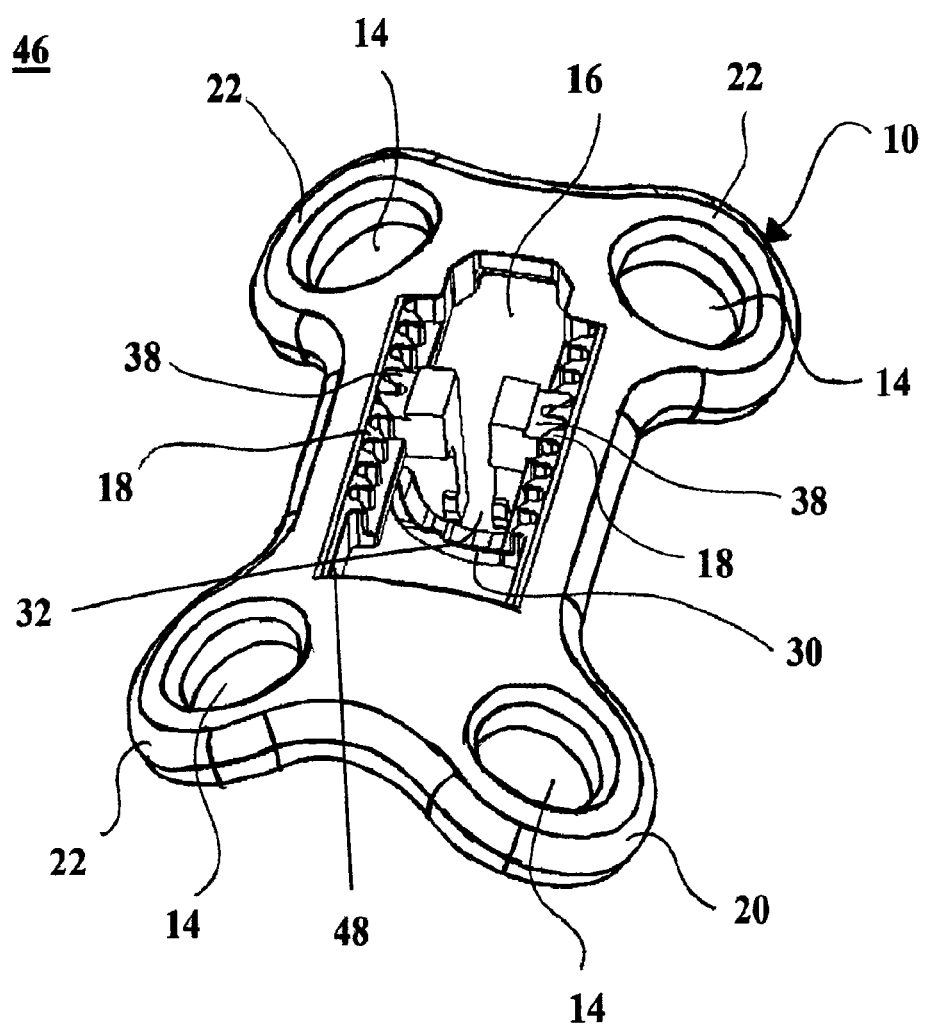
FIG. 12 is an isometric view of the ratcheting plate of FIGS. 1-5 and the ratcheting tab of FIGS. 6-10 inserted into the ratcheting plate, in accordance with an aspect of the present invention.
Figure 13:
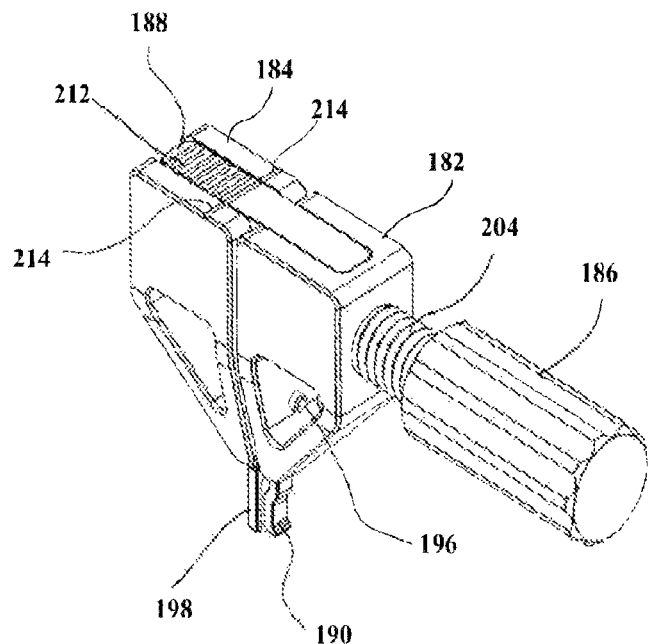
FIG. 13 is an isometric view of a first tool used to actuate a ratcheting plate and tab assembly, in accordance with an aspect of the present invention.
Figure 14:
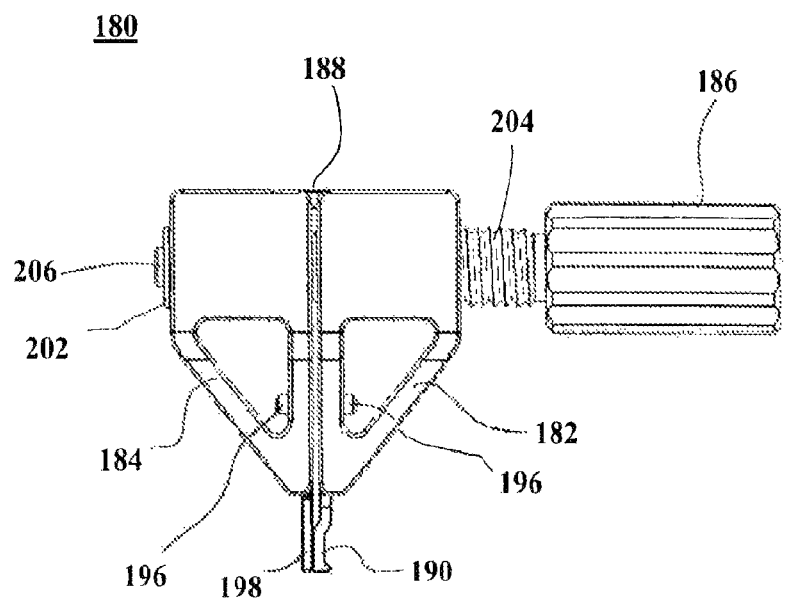
FIG. 14 is a side view of the tool of FIG. 13, in accordance with an aspect of the present invention.
Figure 16A:
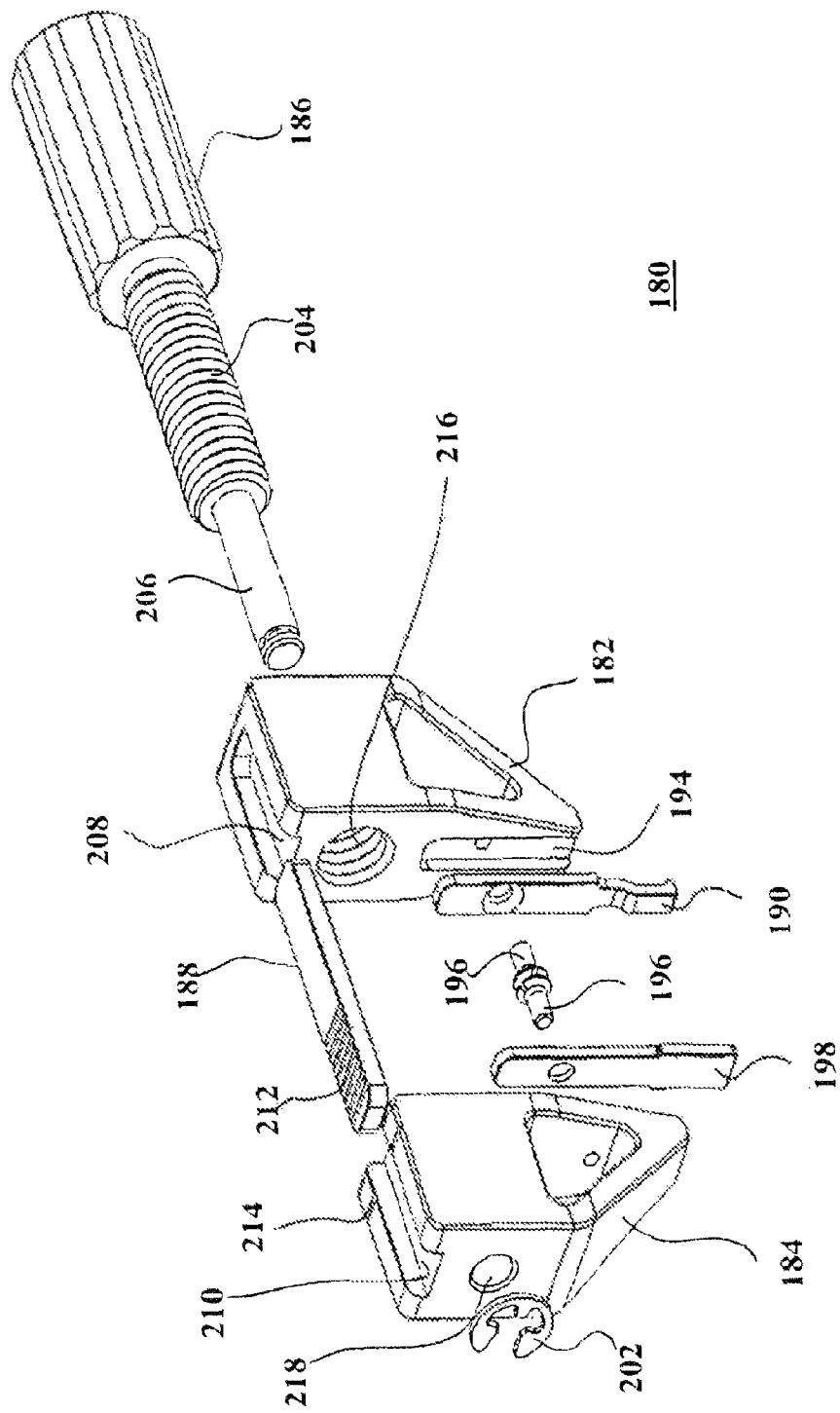
FIG. 16A is an exploded left isometric view of the tool of FIGS. 13-15, in accordance with an aspect of the present invention.

As best seen in FIGS. 11 and 12, a plate and tab assembly 46 are shown. The tab 30 may be inserted into the plate 10 by squeezing the indents 40 and sliding tab 30 into place within the opening 16 of the plate 10. Alternatively, the tab 30 may be inserted into the plate 10 by rotating the tab 30 ninety degrees, inserting the tab 30 into opening 16, and then again turning the tab 30 ninety degrees to engage the teeth of the longitudinal rails 18 of the plate 10. As the indents 40 are squeezed the central slot 32 allows for deflection of the arms 34 thereby decreasing the width of the tab 30. When the teeth 38 of the tab 30 are aligned with the teeth 18 of the plate 10 the indents 40 may then be released and the teeth 38 interlock with teeth 18. Once the desired distraction has been achieved and the plate 10 is secured to the bone surfaces, bone may be inserted around the tab prior to closing the incision in the patient. It is also contemplated that the tab 30 may be removed from the plate 10 before the patient is closed. The tab 30 may be removed from plate 10 by rotating the tab 30 ninety degrees to release the teeth 38 from teeth 18 and removing the tab 30 from the plate 10. Alternatively, the tab 30 may be removed from plate 10 by moving the tab into a gap 48 where there are no teeth 18 along the opening 16 of the plate 10. The method of distraction using the plate 10 and tab 30 will be discussed in greater detail below with reference to FIGS. 20-22.

Referring now to FIGS. 13-16B, a first embodiment of tool 180 is shown. The tool 180 has a first arm 182 and a second arm 184. The first arm 182 may have a first tab 190 secured in a first cavity 194 with a fastener 196 and the second arm 184 may have a second tab 198 secured in a second cavity 200 with a fastener 196. The tool 180 also has a knob 186 which passes through an opening 216 in the first arm 182 and an opening 218 in the second arm 184. The first arm 182 and second arm 184 are secured onto the knob 186 by a retaining ring 202. The knob 186 also has a first end 204 which mates with the opening 216 in the first arm 182 and a second end 206 which mates with the opening 218 in the second arm 184. In the preferred depicted embodiment, the first end 204 may be threaded and the second end 206 may be smooth. In addition, the first end 204 may have a larger diameter than the second end 206. Likewise, the opening 216 may be threaded and may have a larger diameter than the opening 218. The tool 180 may also have an alignment bar 188. The alignment bar 188 is removably fitted in a second cavity 208 on the first arm 182 and slidably inserted into a third cavity 210 on the second arm 184. The alignment bar 188 has indicator lines 212. The indicator lines 212 on the alignment bar 188 align with the indicator lines 214 on the second arm 184 to enable the user to measure how far the second tab 198 has been moved from the first tab 190 by turning knob 186. The indicator lines 212 may be set at a certain distance, such as 0.1 mm to 1 mm, more preferably at 0.5 mm, and most preferably at 1.0 mm, apart allowing the surgeon to see how far the tab 30 has been moved along the opening 16 of plate 10.

Figure 17:
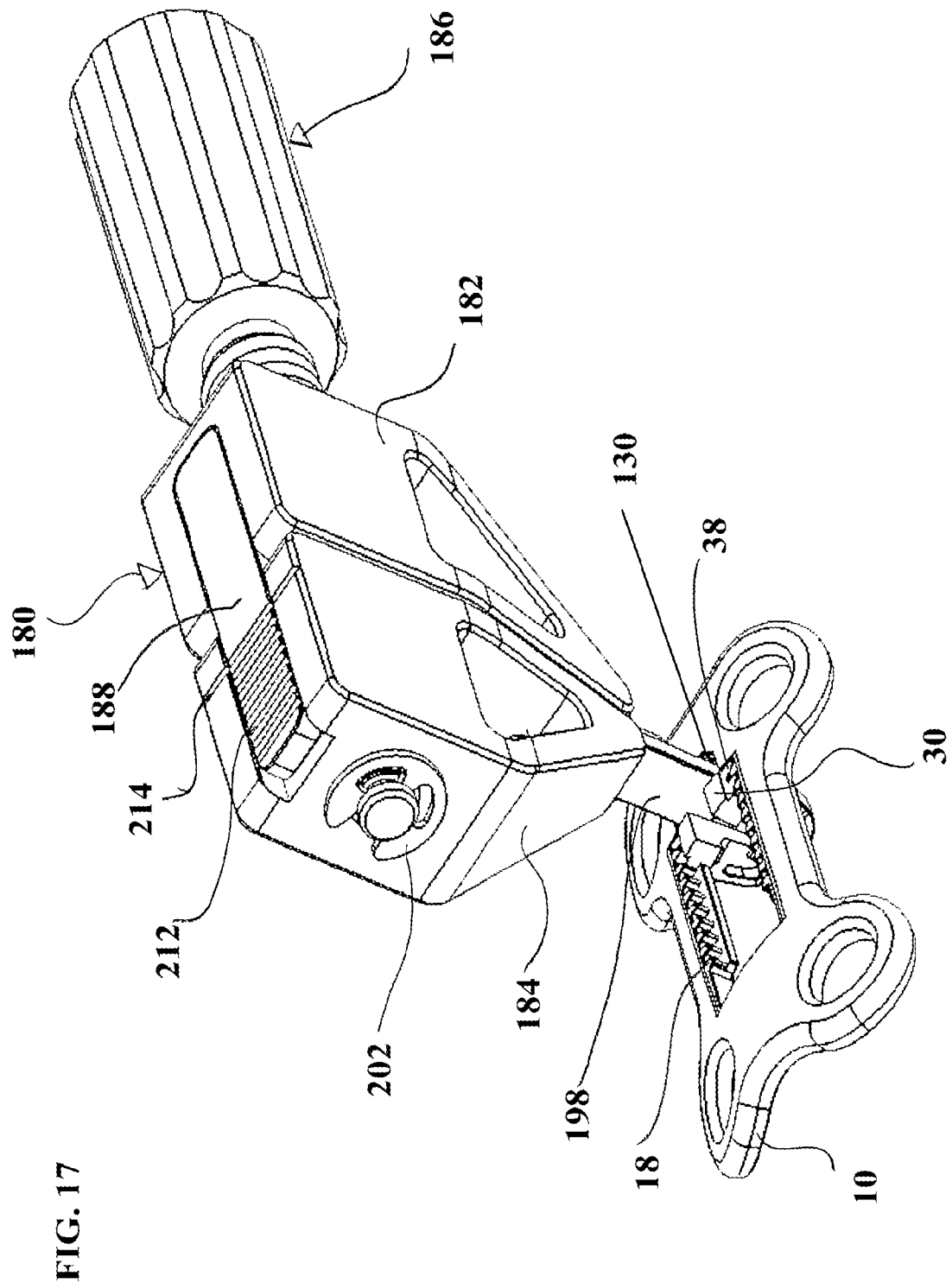
FIG. 17 is an isometric view of the tool of FIGS. 13-16B and the plate and tab assembly of FIG. 11-12 in a retracted position, in accordance with an aspect of the present invention.
Figure 18:
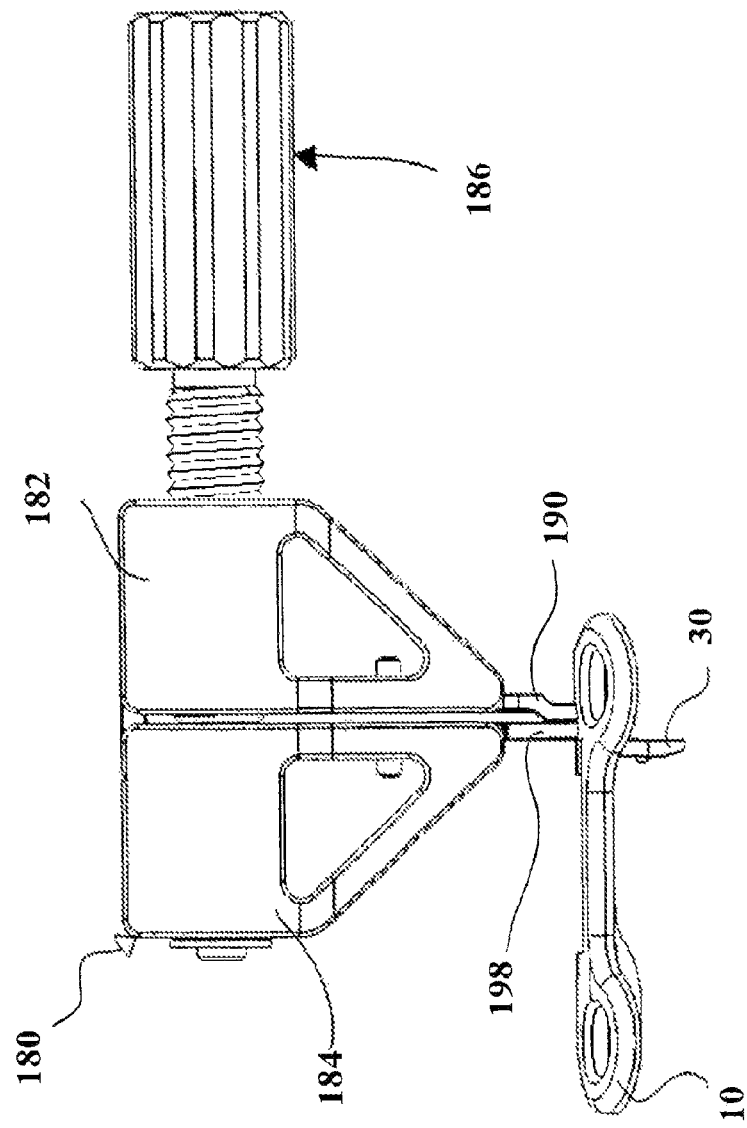
FIG. 18 is a side view of the tool and plate and tab assembly of FIG. 17, in accordance with an aspect of the present invention.
Figure 19:
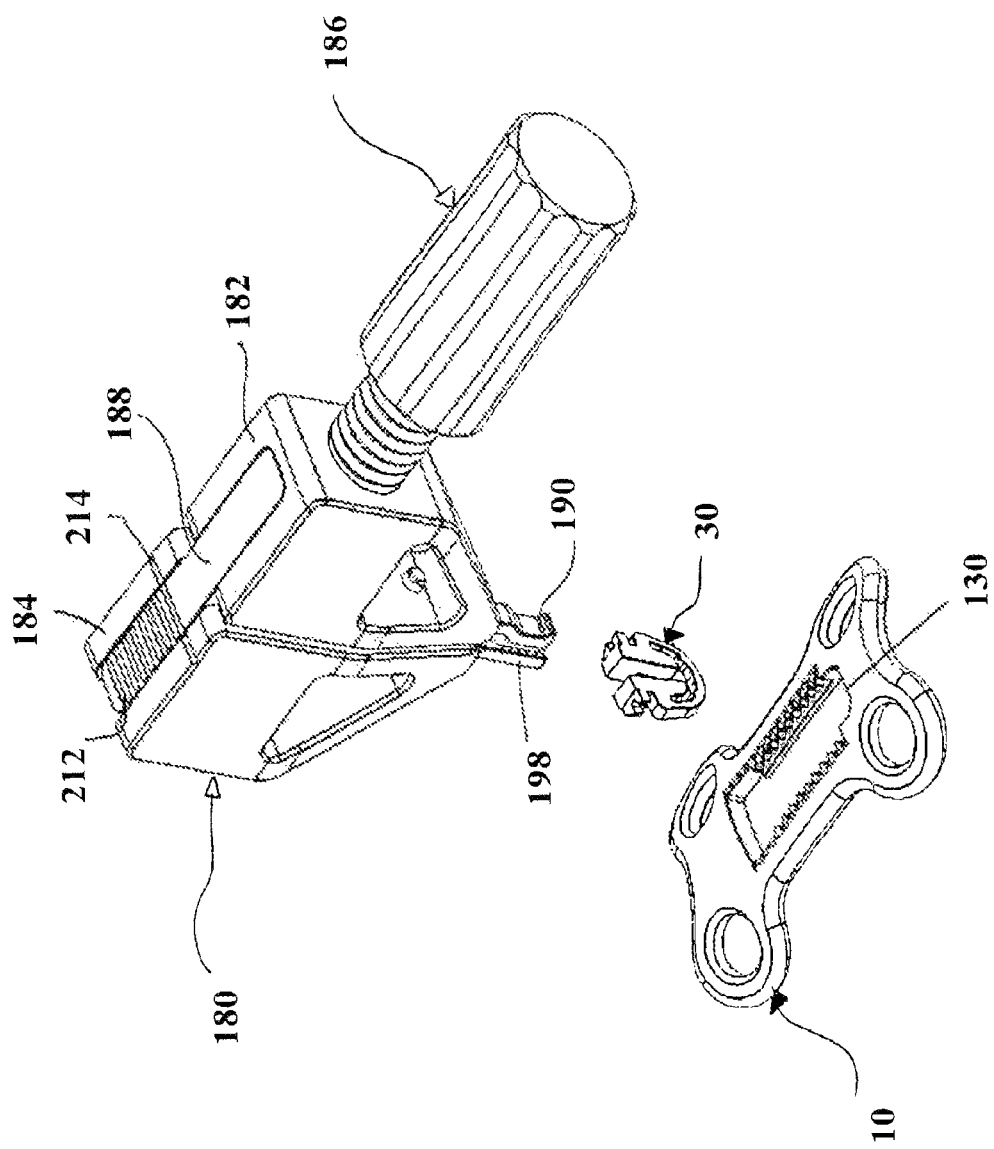
FIG. 19 is a partially exploded isometric view of the tool and plate and tab assembly of FIGS. 17-18, in accordance with an aspect of the present invention.

Illustrated in FIGS. 17-19 is how the tool 180, the plate 10, and the tab 30 function together. The first tab 190 and second tab 198 in a retracted position are inserted into an opening 130 between the plate 10 and the tab 30. The first tab 190 mates with the plate 10 and the second tab 198 mates with the tab 30. When the knob 186 is turned, the second arm 184 is forced away from the first arm 182 moving the tab 30 along the teeth 18 of plate 10. As the first tab 190 and second tab 198 displace the first arm 182, the second arm 184 will also be displaced. The alignment bar 188 which is fixed in the first arm 182 slides along the third cavity 210 as the first arm 182 and second arm 184 are displaced. As the alignment bar 188 slides along the third cavity 210, the indicator lines 212 show the surgeon how far the second arm 184 has separated from the first arm 182 thereby providing the distance the two bones contacting the first tab 190 and second tab 198 have moved relative to each other.

Figure 20:
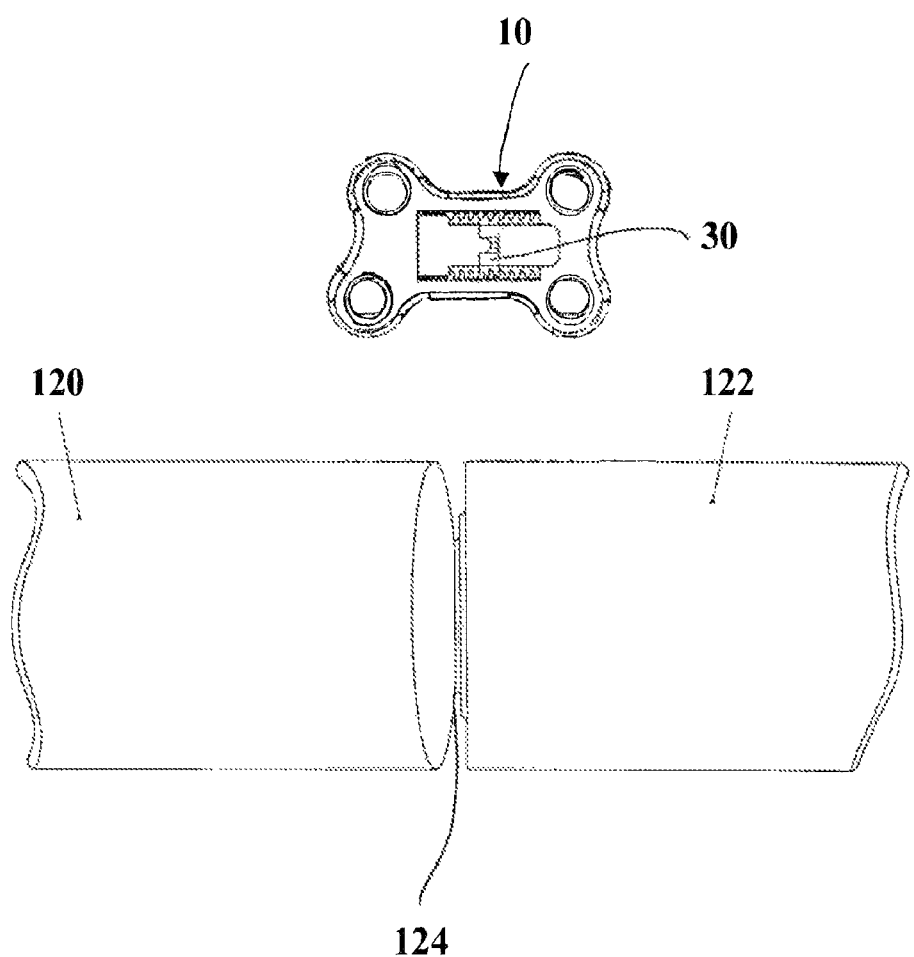
FIG. 20 is a top view of the ratcheting plate and tab assembly of FIGS. 11 and 12 and two bone segments, in accordance with an aspect of the present invention.
Figure 21:
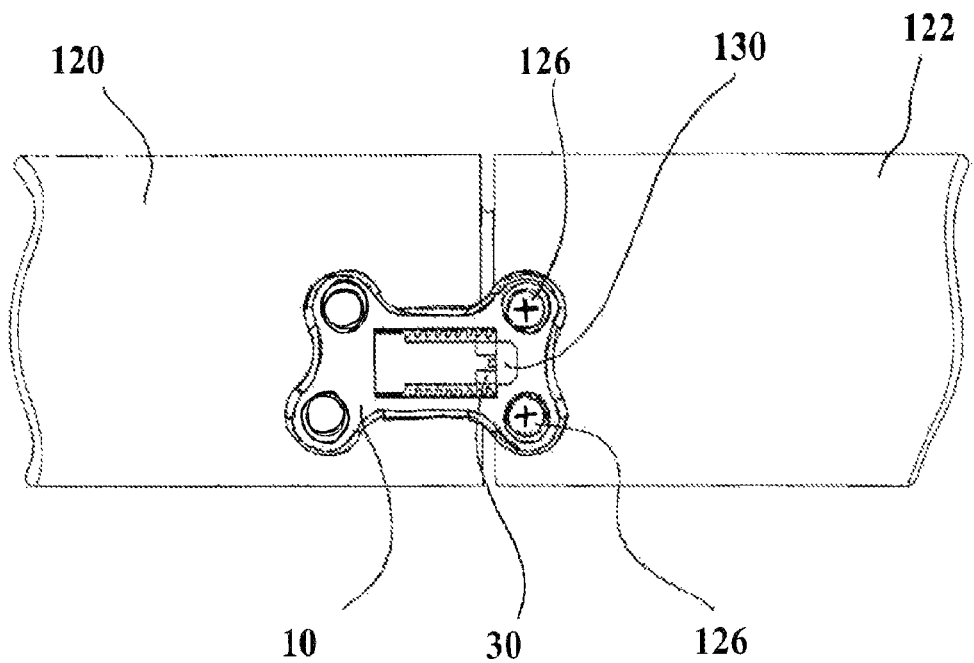
FIG. 21 is a top view of the ratcheting plate and tab assembly and two bone segments of FIG. 20, wherein the ratcheting tab is inserted between the two bone segments and the ratcheting plate is attached to a first bone segment in an initial position, in accordance with an aspect of the present invention.
Figure 22:
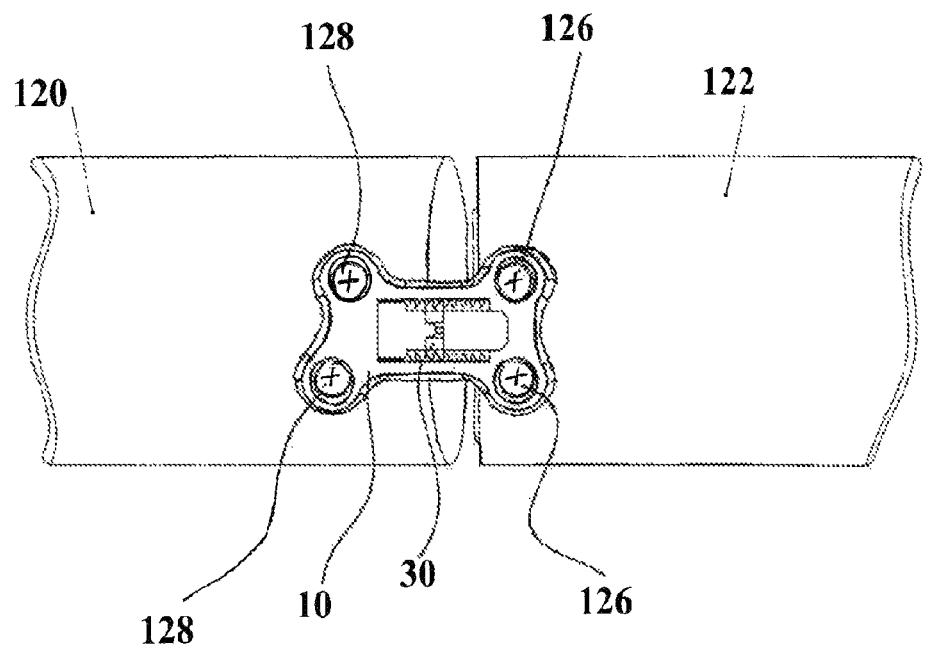
FIG. 22 is a top view of a ratcheting plate and tab assembly and two bone segments of FIGS. 20-21 attached to the first and second bone segments in an actuated position, in accordance with an aspect of the present invention.
Figure 23:
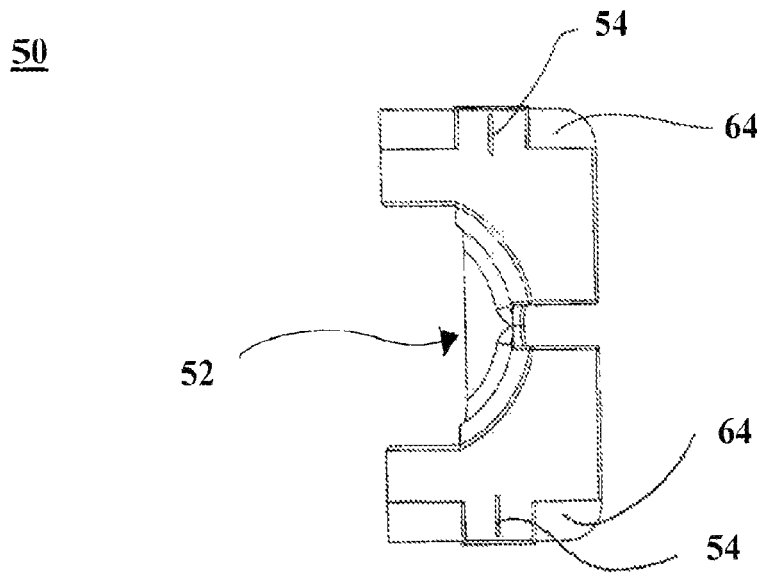
FIG. 23 is a top view of a second embodiment of a ratcheting tab, in accordance with an aspect of the present invention.
Figure 24:
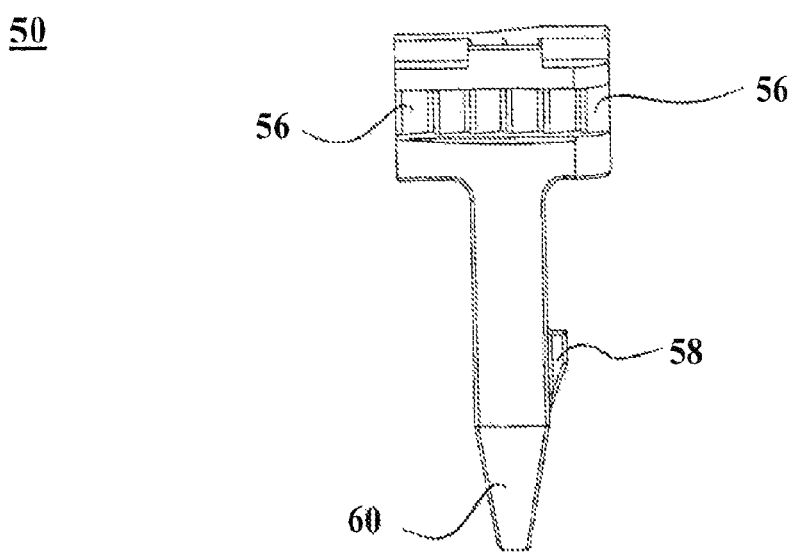
FIG. 24 is a side view of the ratcheting tab of FIG. 23, in accordance with an aspect of the present invention.
Figure 25:
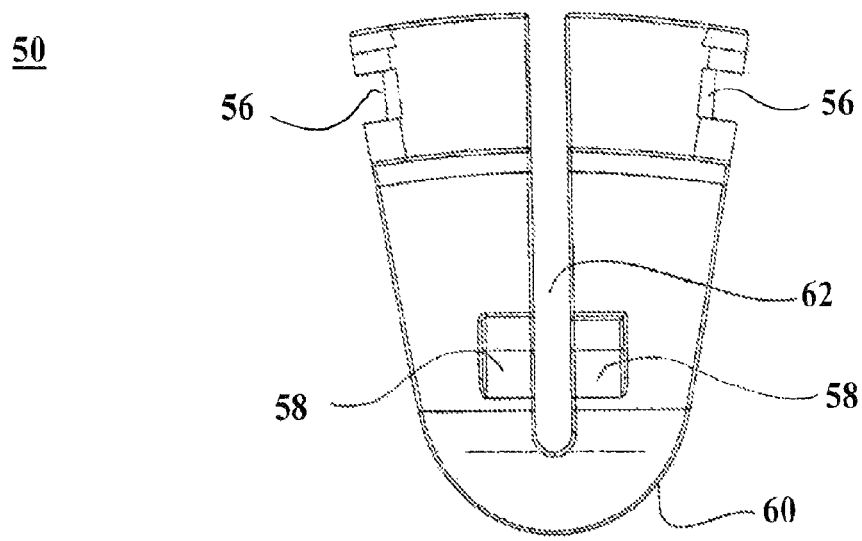
FIG. 25 is a front view of the ratcheting tab of FIGS. 23 and 24, in accordance with an aspect of the present invention.
Figure 26:
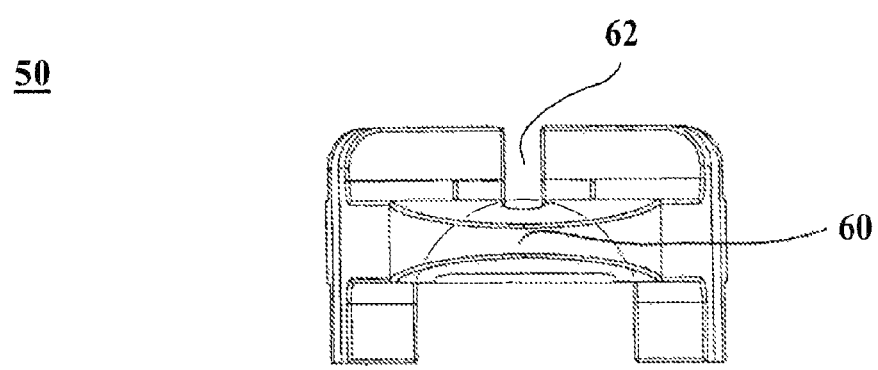
FIG. 26 is a bottom view of the ratcheting tab of FIGS. 23-25, in accordance with an aspect of the present invention.
Figure 27:
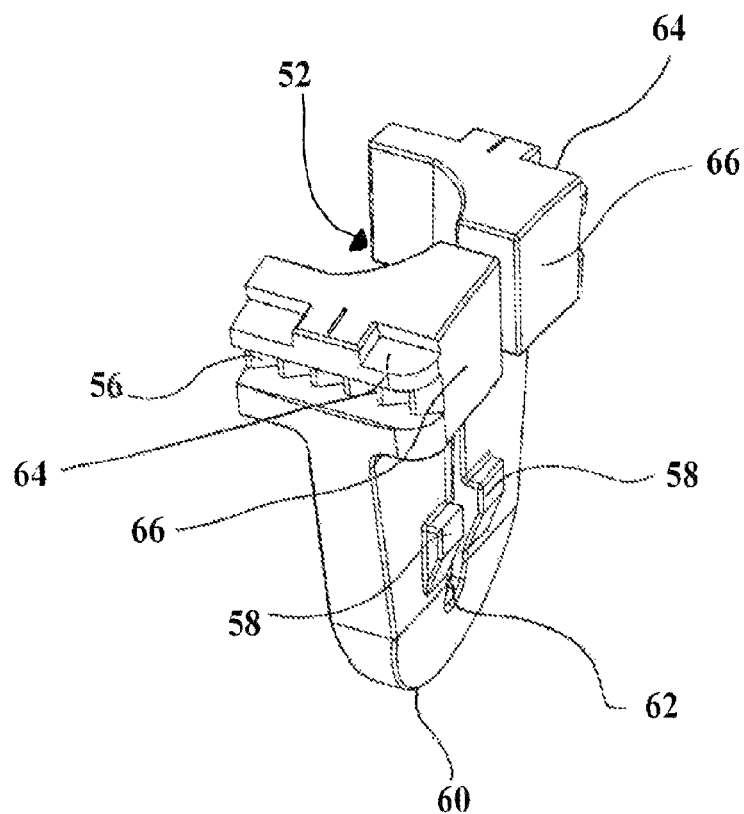
FIG. 27 is an isometric view of the ratcheting tab of FIGS. 23-26, in accordance with an aspect of the present invention.

Referring now to FIGS. 20-22, the tab 30 in the plate 10 and a first bone surface 120 and a second bone surface 122 are shown. The plate 10 has tab 30 in a center position in FIG. 20. The first bone surface 120 and second bone surface 122 may be two separate bones or one bone that has been osteotomized or fractured. During surgery the surgeon will make an incision in the patient and perform an osteotomy on the bone or bones requiring correction. During the osteotomy the first bone 120 may be cut leaving the first bone 120 connected by a second portion of bone 124 which acts as a hinge. For example, with reference to the foot bones the hinge would be intact lateral cortex, but may also be opposite cortex from other bones. The plate 10 with the tab 30 may then be inserted by being slid into place between the bone or bones created by the osteotomy. After the plate 10 and tab 30 are positioned in a desired position over the first bone 120 and second bone 122 and within the osteotomy, the plate 10 may be fastened at the proximal end to the bone using fasteners. The plate 10 and tab 30 may be attached with two fasteners 126 to the second bone 122. The fasteners 126 may be screws, nails, pins, staples, or the like. When the plate 10 is attached to the second bone 122, the tab 30 is between the first bone 120 and second bone 122 in an initial position at the proximal end of the plate 10. The first bone 120 will also generally be in an initial position when the plate 10 and tab 30 are inserted. Although not shown, the tool 180 may then be inserted into the opening 130 to advance the tab 30 toward the distal end of the plate 10 thereby displacing the first bone 120 from the second bone 122 at a desired distance. As the tab 30 is advanced towards the distal end of the plate 10, the teeth 38 of the tab 30 ratchet over the teeth 18 of the plate 10. The teeth 38 of the tab 30 and teeth 18 of the plate 10 may prevent the tab 30 from being forced back towards the opening 130 by the force of the bones being distracted. As the teeth 38 of tab 30 ratchets over the teeth 18 of the plate 10 the protrusions 42 engage underneath the cortex of the first bone 120 and a force is applied to the first bone 120. As the teeth 38 continue to ratchet over the teeth 18 of plate 10 the first bone 120 is separated farther from the second bone 122 until a desired separation is reached.

Referring now to FIG. 22, the first bone 120 and second bone 122 are in a distracted position where the tab 30 has been advanced along the teeth 18 of plate 10 to a desired distance. Once the first bone 120 and second bone 122 are distracted a desired distance, two fasteners 128 may then be inserted through the openings 14 into the first bone 120 to secure the plate 10 in place on the first bone 120 and second bone 122 at the desired distraction. The fasteners 128 may be screws, nails, pins, or the like. Bone may also be inserted into the opening around the plate 10 and tab 30. The surgeon may then close the incision. Optionally, the tab 30 may be removed prior to the surgeon closing the incision.

Figure 28:
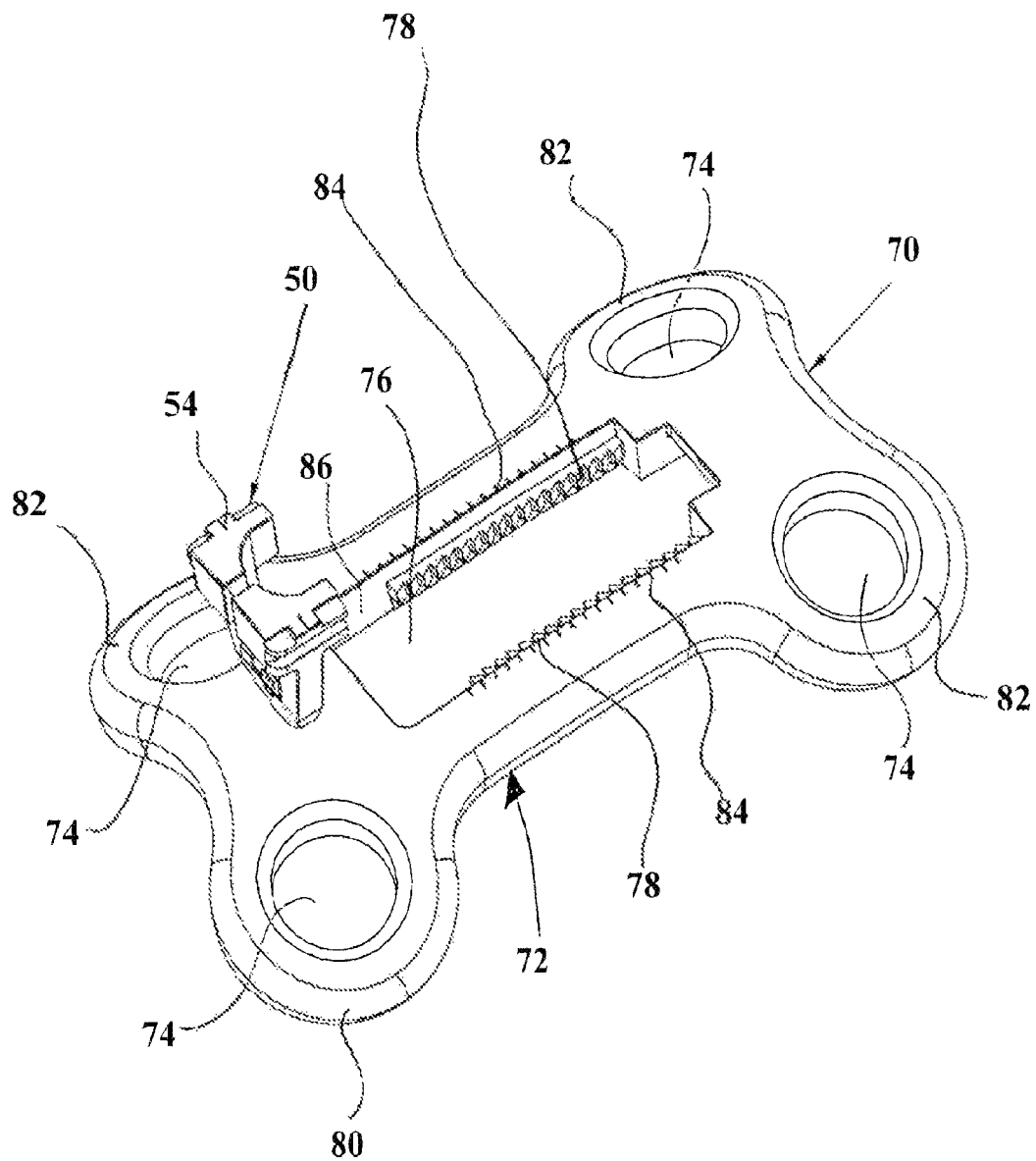
FIG. 28 is an exploded isometric view of a second embodiment of a ratcheting plate and the ratcheting tab of FIGS. 23-27, in accordance with an aspect of the present invention.
Figure 29:
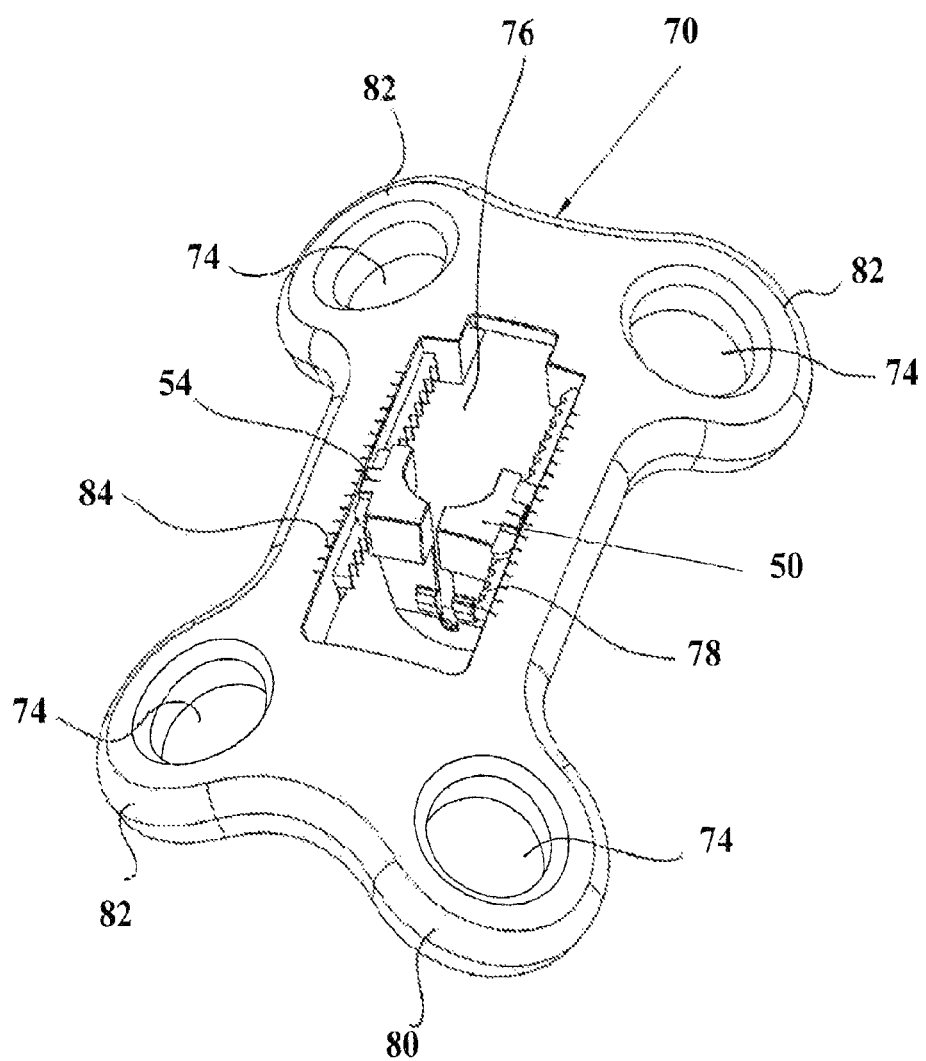
FIG. 29 is an isometric view of the second embodiment ratcheting plate and the ratcheting tab of FIGS. 23-27 inserted into the second embodiment ratcheting plate, in accordance with an aspect of the present invention.

Referring now to FIGS. 23-27, a second embodiment of a ratcheting tab 50 is shown. The ratcheting tab 50 has a cutout 52 for receiving a tool for actuation. The cutout 52 is illustrated as a semi-circular cutout although other shapes, such as squares, rectangles, ovals, and the like, are also contemplated. The top of the tab 50 also has two arms 66 which have indicator lines 54 for showing the position of the tab 50 relative to the plate 10. The two arms 66 of the tab 50 may also have inset ratcheting teeth 56 for mating with a plate 70 as best seen in FIGS. 28-29 and described in greater detail hereinafter. The tab 50 may also have protrusions 58 on either side of a central slot 62. The protrusions 58 may engage the bone during distraction and may more preferably engage the bottom surface of the cortical bone. The tab 50 may also have indents 64 on the top of the tab 50. The indents 64 enable a tool, (Not Shown), to engage the top of the tab 50 and when squeezed the central slot 62 allows for deflection of the sides of tab 50 enabling the teeth 56 to disengage from the teeth 78 of a plate 70 and the tab 50 to be released. The tab 50 may also have a tapered end 60 for assisting in the insertion of the tab 50 between two bone surfaces.

The second embodiment of a ratcheting plate 70 and the tab 50 are depicted in FIGS. 28-29. The ratcheting plate 70 has a body 72 with one or more screw holes 74 and an opening 76. The plate 70 may be generally I-shaped with a generally rectangular shaped body 72 and has two sets of rounded arms forming the top and bottom lines of the I-shape. Other shaped plates 70 are also contemplated including but not limited to generally H-shape plates. The first pair of rounded arms of the body 72 may have a first arm 80, which is offset from a second arm 82 and the second pair of rounded arms of the body 12 may have two parallel second arms 82. The one or more screw holes 74 may be located in the arms 80, 82 of the body 72, wherein there are preferably four screw holes 74. The one or more screw holes 74 may be threaded or non-threaded holes. The opening 76 may be centered in the body 72 along the longitudinal axis of the plate 70. The opening 76 may also have two parallel rows of teeth 78 along the outer edges of the longitudinal side of the opening 76. The plate 70 may also have indicator lines 84 which correspond to the position of the teeth 78. The plate 70 may have a longitudinal curvature for conforming to the angle of the bone or bones it is attached to for distraction. In addition, the plate 70 may have a diametral curvature for conforming to the surface of the outer diameter of the bone or bones which the plate 70 is attached to for distraction.

As shown in FIG. 28, the ratcheting tab 50 may be inserted into the plate 70 by inserting the tab 50 into a gap 86 where there are no teeth 78 along the opening 76 of the plate 70. After the tab 50 is inserted into the gap 86 the indents 64 may be squeezed allowing the central slot 62 to deflect so the teeth 56 may interlock with the teeth 78. When the teeth 56 of the tab 50 are aligned with the teeth 78 of the plate 70 at the desired position the indents 64 may then be released allowing the teeth 56 to interlock with teeth 78. When the teeth 56 are interlocked with the teeth 78 the indicator lines 54 of the tab 50 are aligned with an indicator line 84 on each side of the plate 70. The indicator lines 84 may also be set at a certain distance, such as 0.5 mm, apart allowing the surgeon to see how far the tab 50 has been moved along the opening 76. Once the desired distraction has been achieved and the plate 70 is secured to the bone surfaces. Optionally, the tab 50 may be removed from the plate 70 prior to the surgeon closing the incision. The tab 50 may be removed from plate 70 by rotating the tab 50 ninety degrees to release the teeth 56 from teeth 78 and removing the tab 50 from the plate 70. Alternatively, the tab 50 may be removed from plate 70 by moving the tab into a gap 86 where there are no teeth 78 along the opening 76 of the plate 70. FIG. 29 depicts the assembled plate 70 and tab 50 with the tab 50 in a central position.

Figure 30:
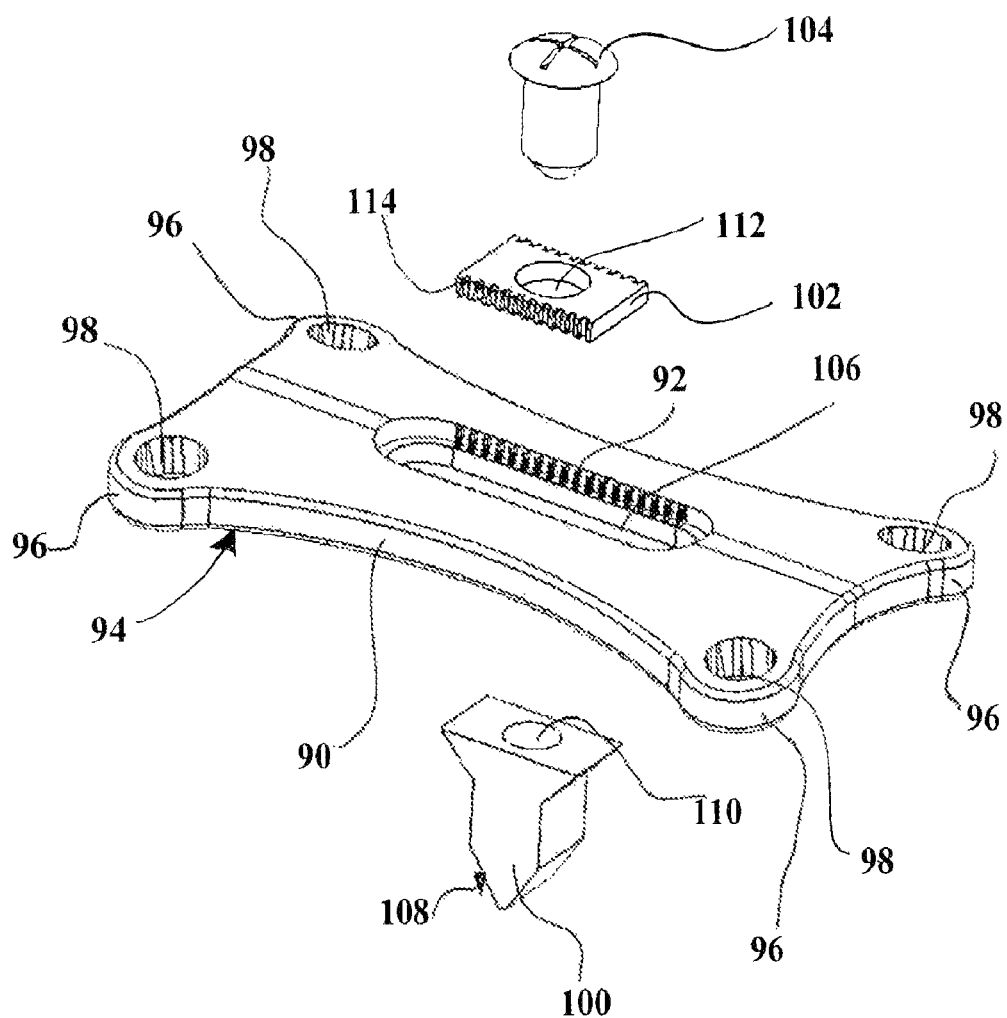
FIG. 30 is an exploded isometric view of a third embodiment of the ratcheting plate and tab assembly, in accordance with an aspect of the present invention.
Figure 31:
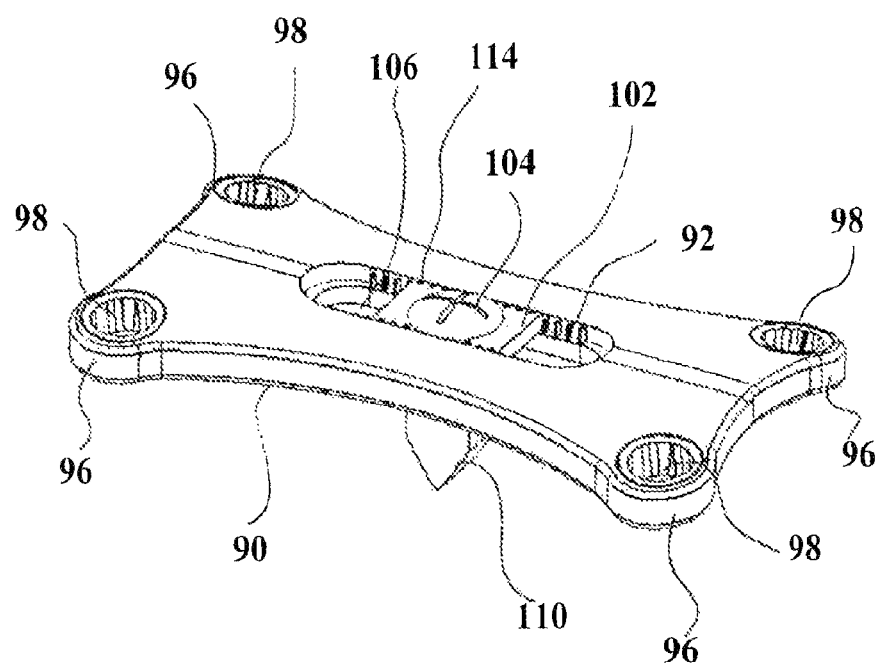
FIG. 31 is an isometric view of the ratcheting plate and tab assembly of FIG. 30, in accordance with an aspect of the present invention.

A third embodiment plate 90 and tab 100 has a locking plate 102 and fastener 104 is best illustrated in FIGS. 30 and 31. The plate 90 is attached to the bones at a predetermined position which is set in advance of inserting the tab 100 and locking plate 102 into the opening 106 of the plate 90. The plate 90 has a body 94 with one or more screw holes 96 and an opening 106. The plate 90 may be generally I-shaped with a generally rectangular shaped body 94 and has rounded tabs forming the top and bottom lines of the I-shape. Although other shapes are contemplated for plate 90. The rounded tabs of body 94 may have at least one tab 96. The one or more screw holes 98 may be located in the tabs 96 of the body 94, wherein there are preferably four screw holes 98. The one or more screw holes 98 may be threaded or non-threaded holes. The opening 106 may be centered in the body 94 along the longitudinal axis of the plate 90. The opening 106 may also have two parallel rows of teeth 92 along the outer edges of the longitudinal side of the opening 106. The plate 90 may have a longitudinal curvature for conforming to the angle of the bone or bones it is attached to for distraction. In addition, the plate 90 may have a diametral curvature for conforming to the surface of the outer diameter of the bone or bones which the plate 90 is attached to for distraction. The tab 100 has a tapered end 108 and an opening 110. The locking plate 102 may have an opening 112 and two parallel sides have teeth 114 for mating with the teeth 92 of the plate 90.

Tab 100 and locking plate 102 are inserted into the plate 90 and the tab 100 is secured to the locking plate 102 with the fastener 104. As illustrated in FIG. 31, the tab 100 is in a central position in the plate 102. When using the plate 90, the surgeon should first position the bone surfaces in the desired position and then the plate 90 may be secured to the bone surfaces at the one or more screw holes 98 using fasteners, such as screws, pins, nails, or the like. In addition when the desired position is obtained the fastener 104 may be inserted to secure the tab 100 and locking plate 102 in the desired position.

Figure 32:
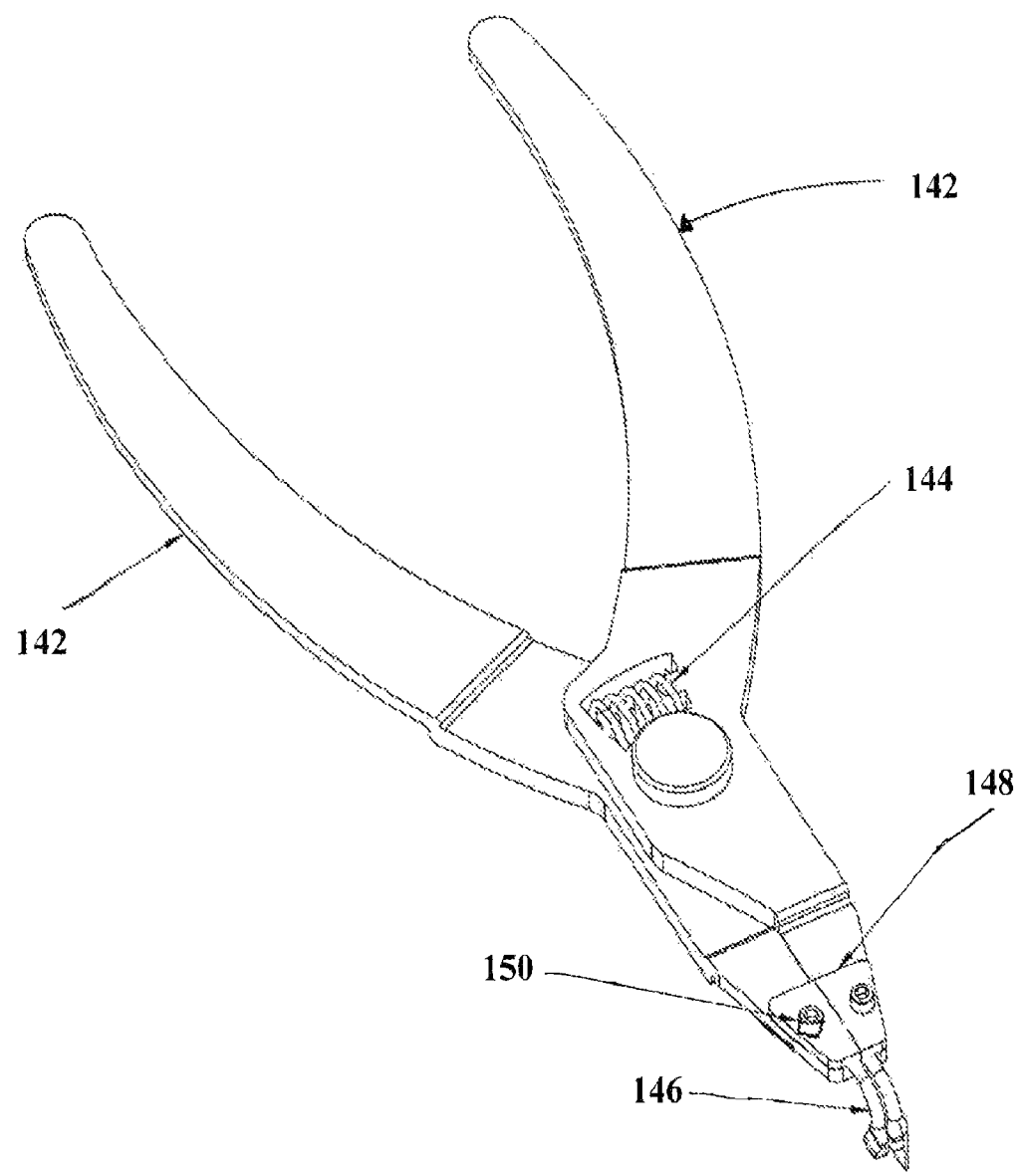
FIG. 32 is an isometric view of a second tool used to actuate a ratcheting plate and tab assembly, in accordance with an aspect of the present invention.
Figure 33:
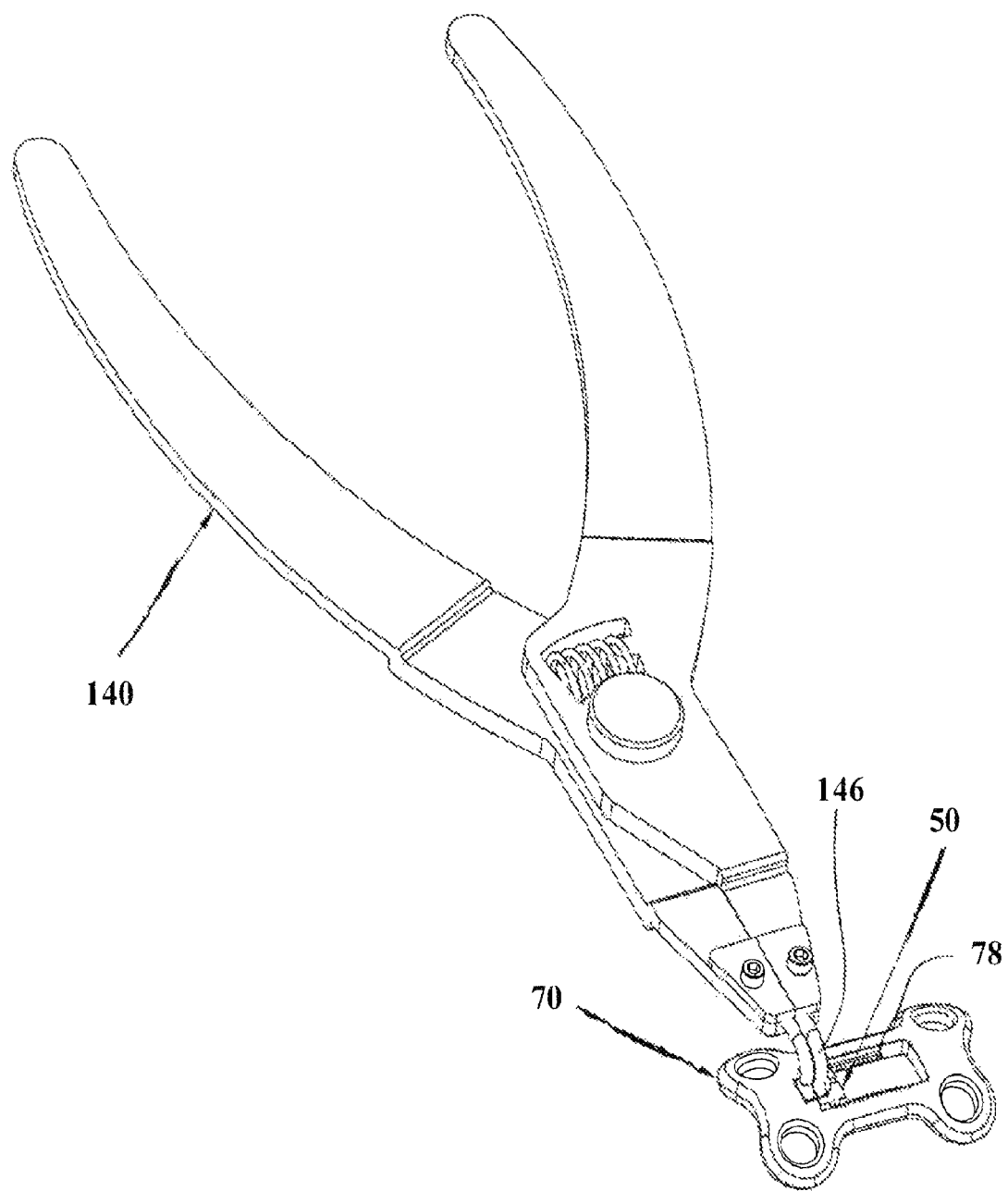
FIG. 33 is an isometric view of the tool of FIG. 32 inserted into the ratcheting plate and tab assembly of FIGS. 28-29, in accordance with an aspect of the present invention.

Referring now to FIGS. 32-33, a second embodiment of tool 140 is shown. The tool 140 has two opposing handles 142 that pivot with respect to each other and a spring 144 which maintains the handles 142 at a desired position. In addition, the tool 140 may have tips 146 that are designed to engage a tab of a plate, such as the tab 30 of plate 10 or the tab 50 of plate 70. The tips 146 may be held in place with plates 148 and fasteners 150. The tips 146 may also be interchangeable to engage various size and shape tabs. The fasteners 150 may be screws, nails, pins, or the like. As best seen in FIG. 33, the tool 140 engages the plate 70 and tab 50 within opening 76 at cutout 52 of the tab 50. The surgeon may then apply force to the handles 142 of the tool 140 to move the tab 50 with respect to plate 70 and along the teeth 78 of plate 70. As the handles 142 are squeezed, the tips 146 separate and force the tab 30 away from the proximal end of the plate 10 thereby separating the two bone surfaces.

Figure 34:
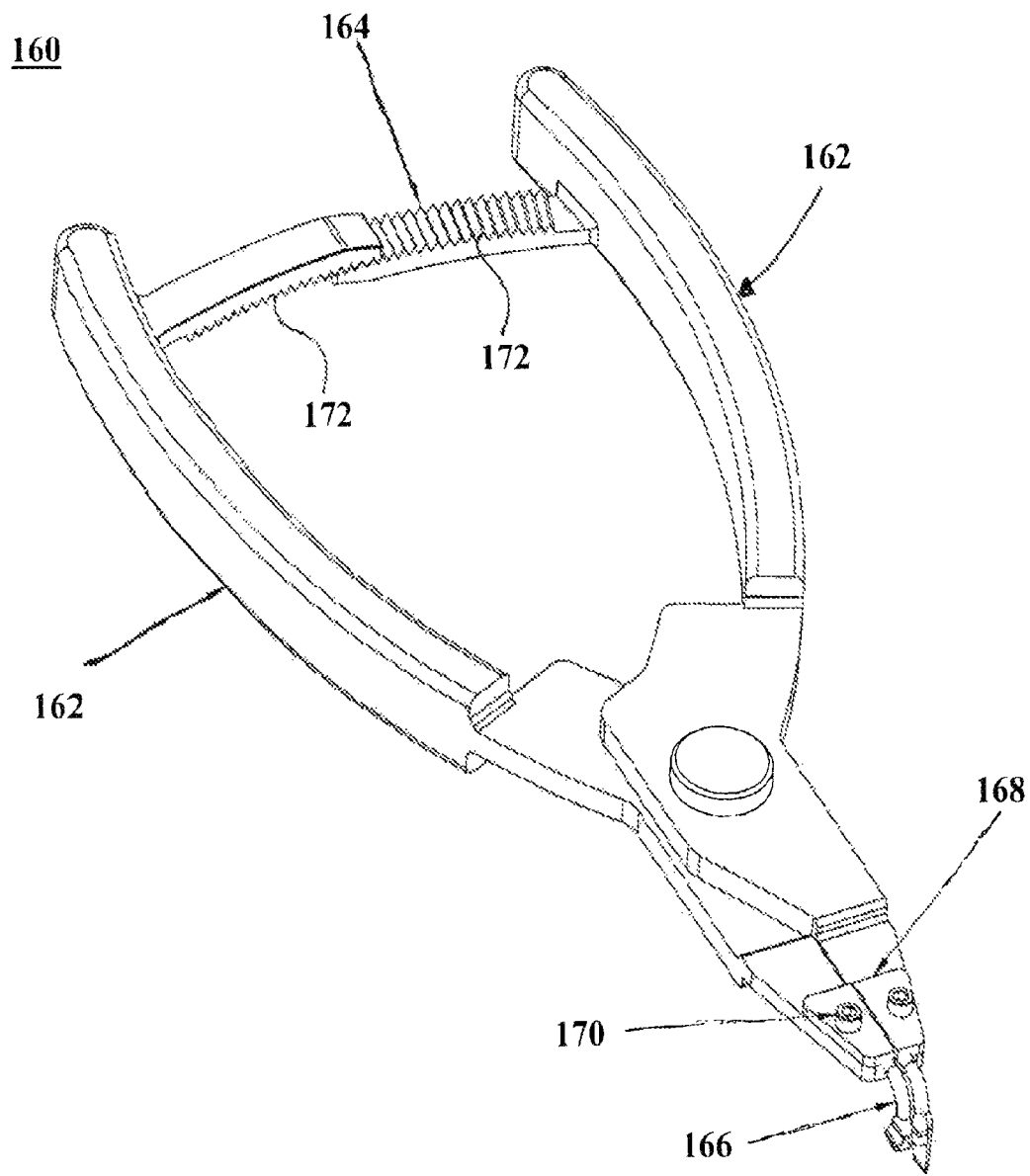
FIG. 34 is an isometric view of a third tool used to actuate a ratcheting plate and tab assembly, in accordance with an aspect of the present invention.
Figure 35:
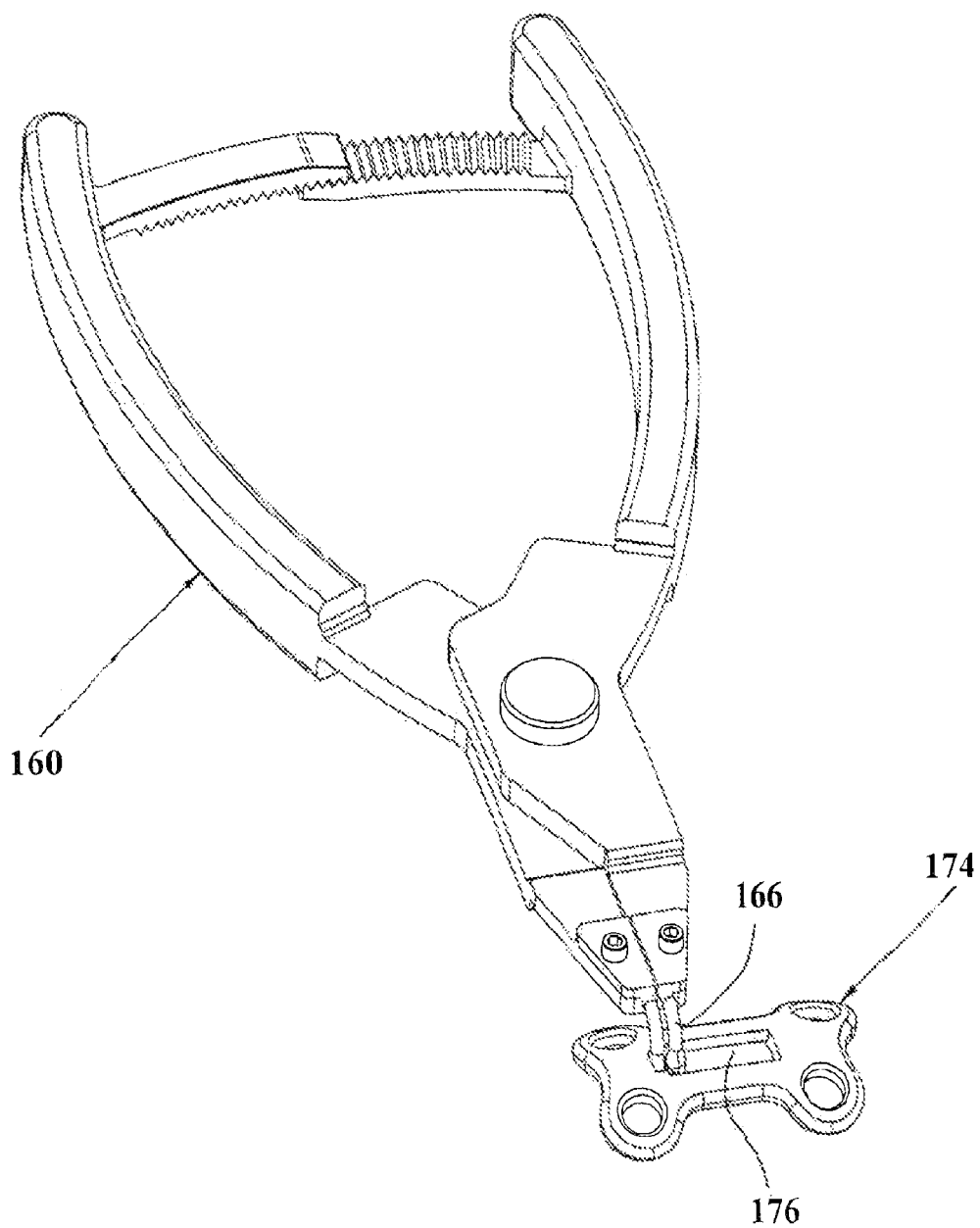
FIG. 35 is an isometric view of the tool of FIG. 34 inserted into a ratcheting plate, in accordance with an aspect of the present invention.

A third embodiment of tool 160 is depicted in FIGS. 34-35. The tool 160 has two opposing handles 162 that pivot with respect to each other and a ratcheting mechanism 164 which maintains the desired position of the handles 162. The ratcheting mechanism 164 has a plurality of teeth 172 to lock the handles 162 in a desired position. The ratcheting mechanism 164 may also be released after a plate 174 is secured in its desired position by applying force to the handles 162 to disengage the teeth 172. The plate 174 has a similar shape to plate 10 and plate 70 discussed above, however plate 174 lacks the teeth of the prior plates in the opening 176. In addition, the tool 160 may have tips 166 that are designed to engage the plate 174 on one side and the bone, not shown, on the opposite side. The tips 166 may be held in place with plates 168 and fasteners 170. The tips 166 may also be interchangeable to provide various sizes and shapes for directly engaging a bone. The fasteners 170 may be screws, nails, pins, or the like. Depicted in FIG. 35 is one of the tips 166 of the tool 160 engaging the plate 174 and the second of the tips 166 engaging a bone surface (Not Shown). In this embodiment, as the handles 162 are squeezed the tips 166 separate, thereby moving the bone away from the proximal end of the plate 174 without the need for a tab.

Figure 36:
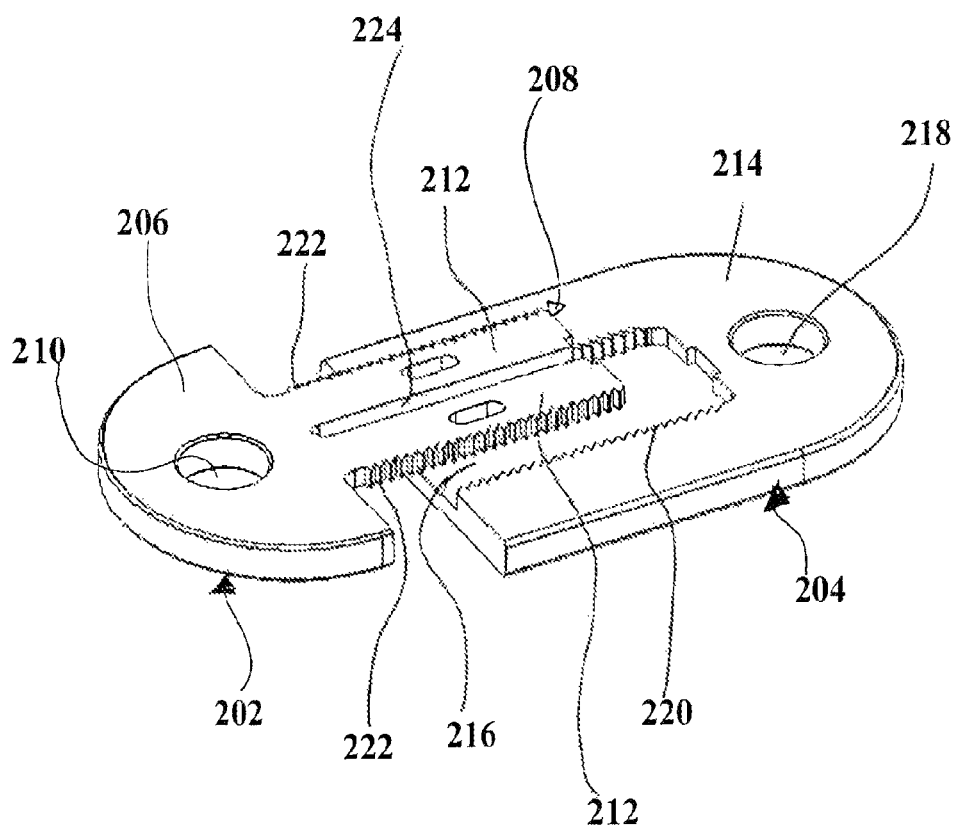
FIG. 36 is an exploded isometric view of a first embodiment of a plate assembly, in accordance with an aspect of the present invention.
Figure 37:
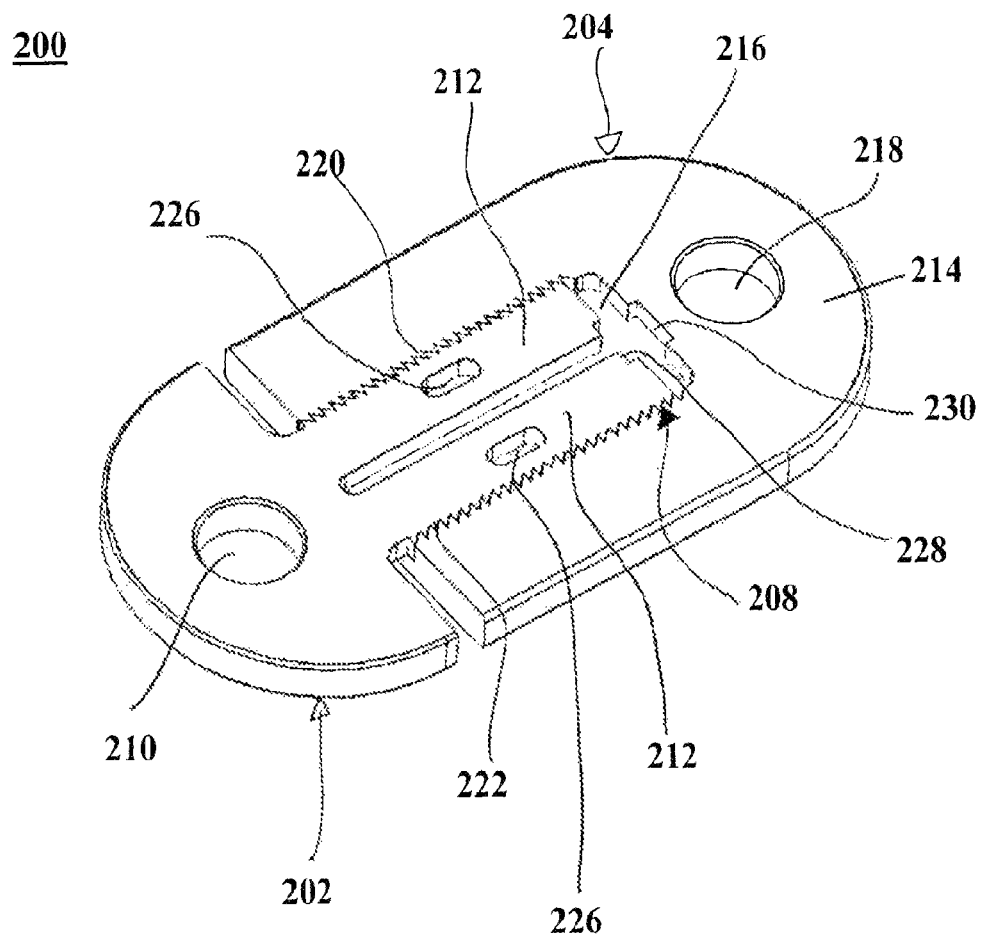
FIG. 37 is an isometric view of the plate assembly of FIG. 36, in accordance with an aspect of the present invention.

Referring now to FIGS. 36-37, a plate assembly 200 is shown. The plate assembly 200 has a male plate 202 and a female plate 204. The male plate 202 has an attachment end 206 and a ratcheting end 208. The attachment end 206 has an opening 210 for securing the male plate 202 to a bone. The ratcheting end 208 has two legs 212 and a row of teeth 222 on the outer surface of the longitudinal sides of each of the two legs 208. The teeth 222 may be one way ratcheting teeth. As depicted in the present embodiment, the teeth 220 and 222 are one way ratcheting teeth for compression. The teeth 220 and 222 are one way ratcheting teeth which may also be aligned for distraction. Alternatively, the teeth 220 and 222 may be two way ratcheting teeth. The female plate 204 has a body 214 with a cavity 216 and an opening 218. The cavity 216 has a generally rectangular shape and two rows of teeth 220 on the inner edges of the longitudinal sides of the cavity 216. The teeth 222 of the male plate 202 mate with the teeth 220 of the female plate 204 and ratchet over each other as a force is applied to the male plate 202. The ratcheting end 208 also has a gap 224 between the two legs 212 which allows for deflection as the ratcheting teeth index. The two legs 212 may also have a recess 226 which enables a tool to be inserted into the ratcheting end 208 to pinch the legs 212 together to release the compression on the legs 212. In addition, the ratcheting end 208 may have a notch 228 and the female plate 204 may have a notch 230. The notches 228 and 230 are opposing and allow for a tool to engage them. When a force is applied to the tool, the male plate 202 and female plate 204 may be forced apart. The male plate 202 and female plate 204 may alternatively have notches for inserting a tool and pulling the male plate 202 and female plate 204 together. As best seen in FIG. 37, the male plate 202 is inserted into the female plate 204 and is partially open.

In use, a surgeon would make an incision in the patient and expose the bone or bones for attachment of the plate assembly 200. Once the bone or bones are exposed, the female plate 204 would be attached to a first bone (Not Shown), and the male plate 202 would be attached to a second bone (Not Shown). The male plate 202 and female plate 204 would be attached with fasteners, such as screws, pins, nails, or the like. The male plate 202 and female plate 204 attached in an initial position with respect to each other and then the male plate 202 and female plate 204 would be ratcheted together for compression or ratcheted apart for distraction. The ratcheting of the male plate 202 and female plate 204 may be done manually, or optionally, a hand tool may be used to assist with the ratcheting.

Figure 38:
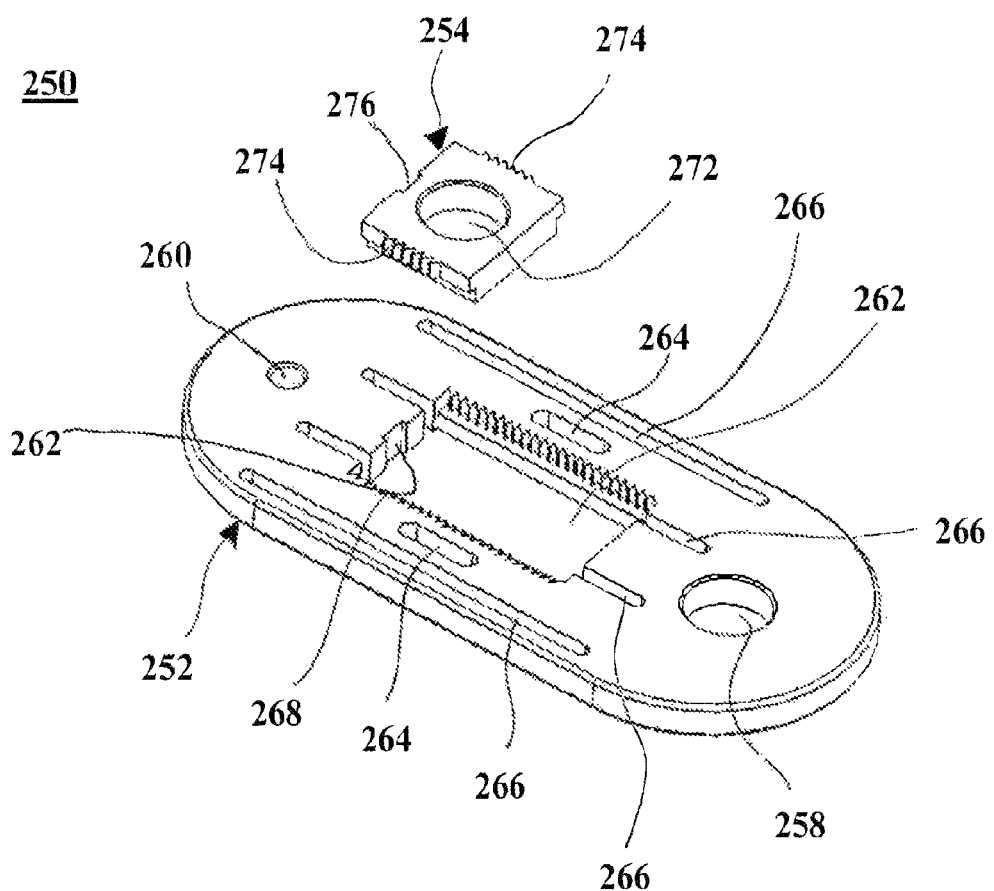
FIG. 38 is an exploded isometric view of a second embodiment of a plate assembly, in accordance with an aspect of the present invention.
Figure 39:
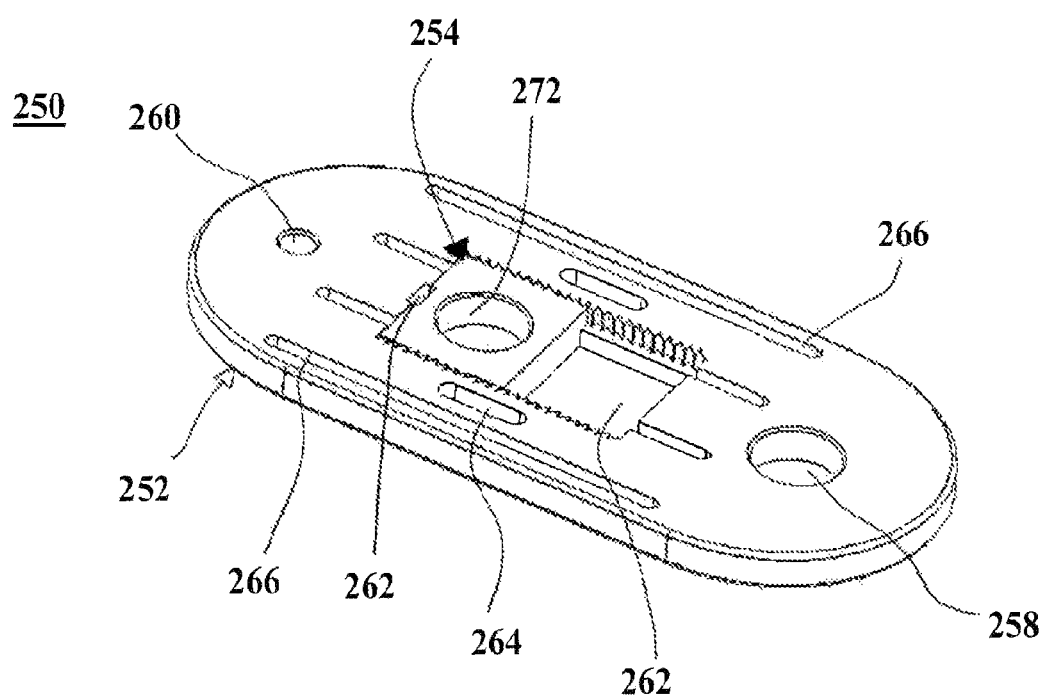
FIG. 39 is an isometric view of the plate assembly of FIG. 38, in accordance with an aspect of the present invention.

A second plate assembly 250 is illustrated in FIGS. 38-39. The plate assembly 250 has a female plate 252 and a male plate 254. The female plate 252 has a body 256 with a first opening 258, a second opening 260, a third opening 262, two notches 264, and at least one elongated slot 266. The third opening 262 has two rows of teeth 268 along the inner edges of the longitudinal sides. The two notches 264 may be used to release the teeth 274 of the male plate 254 from the teeth 268 of the female plate 252. The male plate 254 has a body 270 with an opening 272, two rows of teeth 274 on the outer edges of the longitudinal sides of the body 270, and a notch 276 for ratcheting the male plate 254 within the female plate 252. As best seen in FIG. 39, the male plate 254 is inserted into the female plate 252 in an initial position.

In use, a surgeon would make an incision in the patient and expose the bone or bones for attachment of the plate assembly 250. Once the bone or bones are exposed, the female plate 252 would be attached to a first bone by inserting a fastener in opening 258. The fastener may be a screw, pin, nail, or the like. Then a surgeon may optionally insert a temporary alignment wire (Not Shown), through the opening 260 and into a bone to maintain the position of the female plate 252 while the male plate 254 is inserted into the third opening 262 and secured with a fastener. The fastener may be a screw, pin, nail, or the like. The male plate 254 may then be ratcheted to a desired position. While the male plate 254 is ratcheted, the elongated slots 266 on the female plate 252 allow for the female plate 252 to deflect as the teeth 274 of the male plate 254 ratchet over the teeth 268 of the female plate 252. The male plate 254 and female plate 252 may be ratcheted together for compression or ratcheted apart for distraction. Once a desired position is reached, the ratcheting tool may be removed and the surgeon may close the patient incision.

Figure 40:
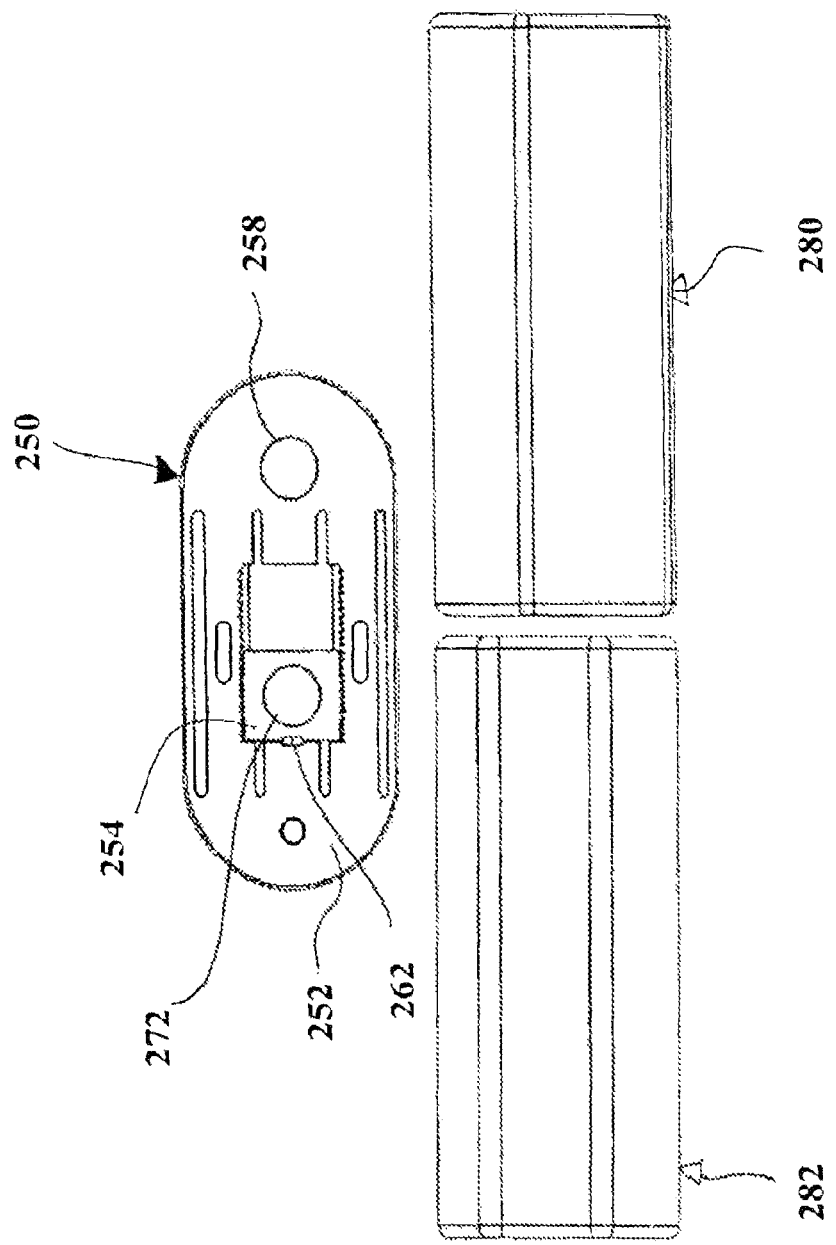
FIG. 40 is a front view of two bones and the plate assembly of FIGS. 38-39, in accordance with an aspect of the present invention.
Figure 41:
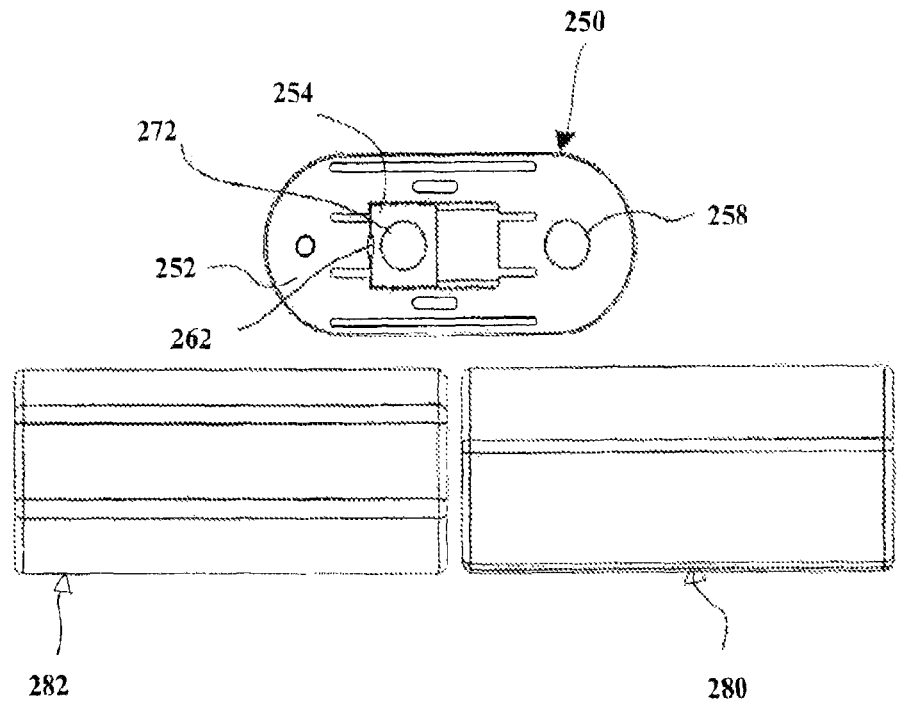
FIG. 41 is a front view of the two bones and the plate assembly of FIG. 40 in the initial mounted position, in accordance with an aspect of the present invention.
Figure 42:
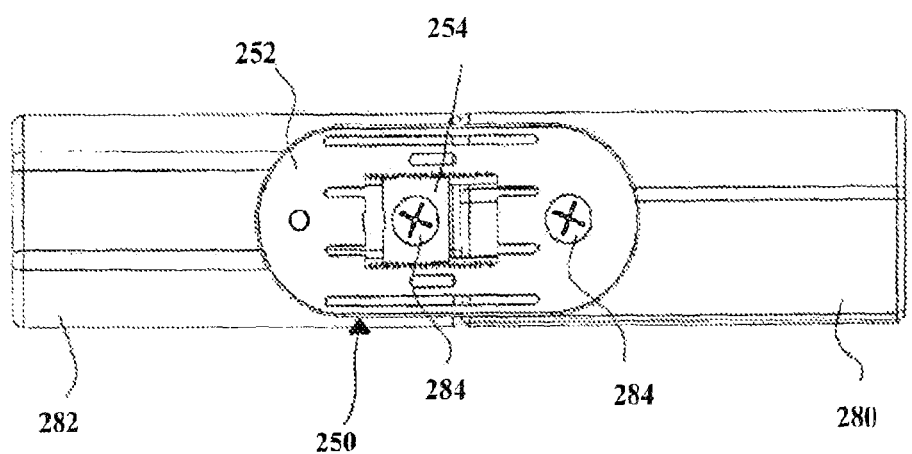
FIG. 42 is a front view of two bones and the plate assembly of FIG. 40 in the actuated position wherein the bones are compressed, in accordance with an aspect of the present invention.

Depicted in FIGS. 40-42 is the plate assembly 250, a first bone 280, and a second bone 282. The plate assembly 250 is attached at the first bone 280 through opening 258 with a fastener 284. As seen in FIG. 41, the male plate 254 is attached to the second bone 282 through opening 272 with a fastener 284 in an initial position. The fastener 284 may be a screw, pin, nail, or the like. In the depicted embodiment, the first bone 280 and second bone 282 are separated by a gap and the plate assembly 250 is assembled for compression. As seen in FIG. 42, the male plate 254 has been ratcheted to a second position where the first bone 280 and second bone 282 have been compressed to close the gap between the first bone 280 and the second bone 282.

Figure 43:
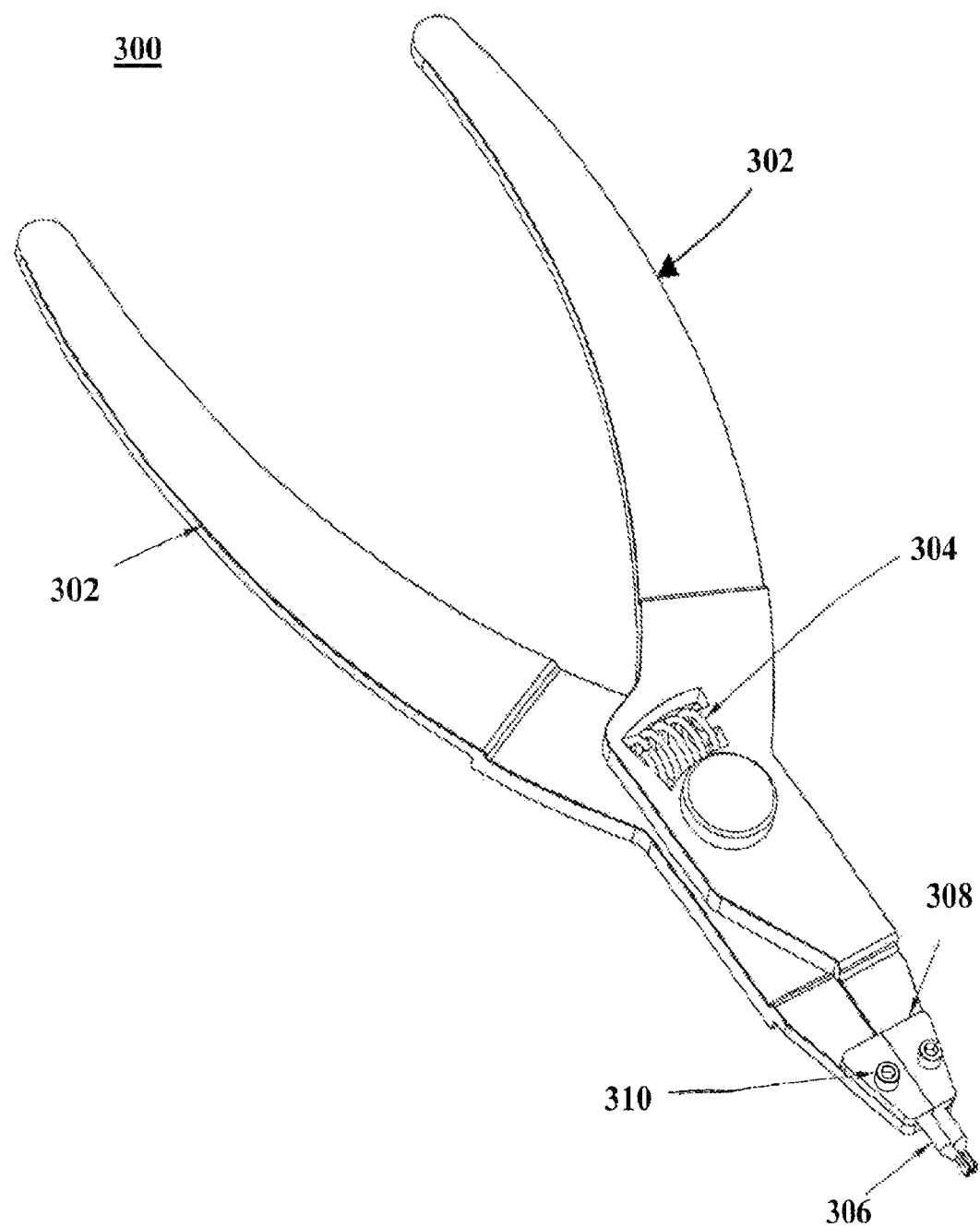
FIG. 43 is an isometric view of one embodiment of a hand tool that is used to actuate the plate of FIGS. 38-39, in accordance with an aspect of the present invention.
Figure 44:
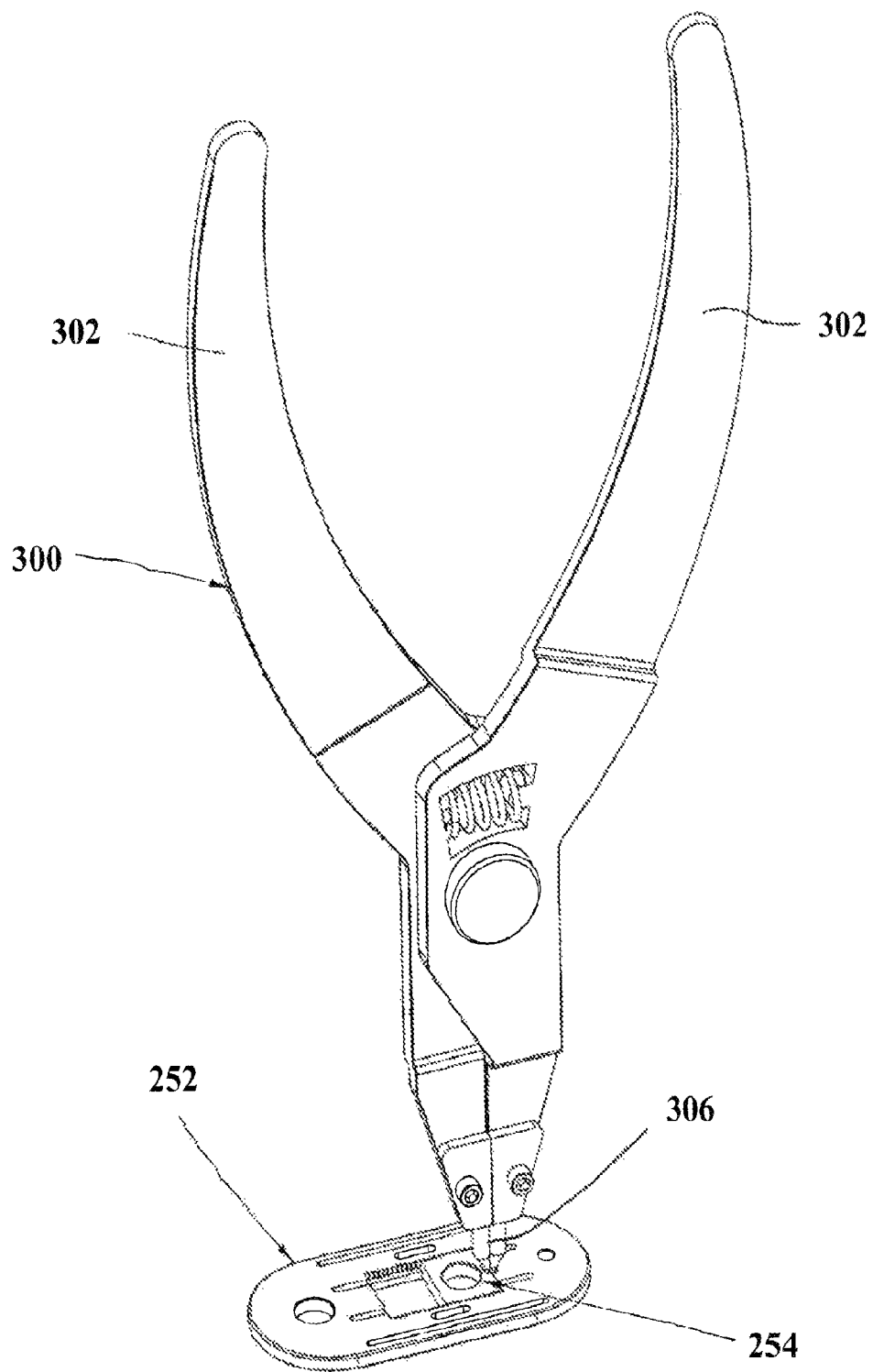
FIG. 44 is an isometric view of the tool of FIG. 43 engaging the plate of FIGS. 38-39, in accordance with an aspect of the present invention.

Referring now to FIGS. 43-44, a tool 300 is shown. The tool 300 has two opposing handles 302 that pivot with respect to each other and a spring 304 which maintains the handles 302 at a desired position. In addition, the tool 300 may have tips 306 that are designed to engage a plate, such as the plate 254. The tips 306 may be held in place with plates 308 and fasteners 310. The tips 306 may also be interchangeable to engage various size and shape plates. The fasteners 310 may be screws, nuts, pins, or the like. As best seen in FIG. 44, the tool 300 engages the plate 254 within notch 276 and the plate 252 in the opening 262. The surgeon may apply a force to the handles 302 of the tool 300 to move the male plate 254 with respect to the female plate 252. As the handles 302 are squeezed, the tips 306 separate and force the male plate 254 down the opening 262 of the female plate 252, thereby compressing the two bones. The tool 300 and plate assembly 250 may be used for compression or distraction of two bones or two bone segments.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method of device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The invention has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the invention be construed as including all such modifications and alterations.

The invention claimed is:

1. An orthopaedic plate system, comprising:
    a plate having a proximal end and a distal end with a central portion extending between the proximal end and the distal end, wherein the plate has a first opening between the proximal end and distal end, a first pair of arms at a proximal end, and a second pair of arms at a distal end; and
    a tab having a body with a first arm and a second arm, wherein the tab is configured to mate with the first opening of the plate and to be inserted between two bone segments, wherein the tab contacts one of the two bone segments to at least one of create or maintain a space between the two bone segments.

2. The plate system of claim 1, wherein the first opening is generally rectangular and has a row of teeth on each longitudinal edge of the first opening.

3. The plate system of claim 2, wherein the first pair of arms have at least one opening for securing the plate to a first bone.

4. The plate system of claim 3, wherein the at least one opening is threaded.

5. The plate system of claim 3, wherein the second pair of arms have at least one opening for securing the plate to a second bone.

6. The plate system of claim 2, wherein the tab has a row of teeth on the first arm and a row of teeth on the second arm.

7. The plate system of claim 6, wherein the row of teeth on each longitudinal edge of the first opening of the plate are configured to engage the row of teeth on the first arm and the row of teeth on the second arm of the tab.

8. The plate system of claim 7, wherein the tab has a notch on the first arm, a notch on the second arm, and wherein the notches may be used to compress the first arm and second arm of the tab to disengage the teeth of the tab.

9. The plate system of claim 2, wherein the central portion has a plurality of markings corresponding to the teeth of the first opening and the tab has at least one marking on the top of the first arm and second arm for aligning with the plurality of markings on the central portion to measure the distance the tab has moved relative to the plate.

10. The plate system of claim 2, wherein the first opening has a gap in the row of teeth on each side of the longitudinal side of the first opening for insertion of the tab.

11. The plate system of claim 1, wherein the plate has a longitudinal axis and a lateral axis.

12. The plate system of claim 11, wherein the plate has a longitudinal curvature along the longitudinal axis.

13. The plate system of claim 12, wherein the plate has a diametral curvature along the lateral axis.

14. The plate system of claim 13, wherein the longitudinal curvature corresponds to a long axis of a bone and the diametral curvature corresponds to a diameter of the bone.

15. The plate system of claim 11, wherein the plate has a diametral curvature along the lateral axis.

16. The plate system of claim 1, wherein the plate is configured as one of a rectangle and I-shaped.

17. The plate system of claim 1, further comprising:
    at least one protrusion on the body of the tab.

18. The plate system of claim 1, wherein the body of the tab is tapered from the first arm and the second arm to a bottom surface of the body.

19. The plate system of claim 1, wherein the body of the tab has a slot.

20. The plate system of claim 19, wherein the slot passes between the first arm and the second arm of the tab and forms an arc at the bottom surface of the tab.

21. The plate system of claim 1, wherein the plate system has a cavity between the plate and the tab for engagement of a tool.

* * * * *